United States Patent [19]

Elsbach et al.

[11] Patent Number: 5,576,292
[45] Date of Patent: Nov. 19, 1996

[54] BIOLOGICALLY ACTIVE BACTERICIDAL/PERMEABILITY-INCREASING PROTEIN FRAGMENTS

[75] Inventors: Peter Elsbach; Jerrold Weiss, both of New York, N.Y.

[73] Assignee: New York University, New York, N.Y.

[21] Appl. No.: 173,968

[22] Filed: Dec. 23, 1993

Related U.S. Application Data

[63] Continuation of Ser. No. 754,204, Aug. 26, 1991, abandoned, which is a continuation-in-part of Ser. No. 621,473, Dec. 3, 1990, abandoned, which is a continuation-in-part of Ser. No. 228,035, Aug. 5, 1988, abandoned, which is a continuation-in-part of Ser. No. 84,335, Aug. 11, 1987, abandoned.

[51] Int. Cl.$^6$ ........................................ A61K 38/16
[52] U.S. Cl. ................................ 514/12; 514/2; 530/324
[58] Field of Search .......................... 514/2, 12; 530/324

[56] References Cited

U.S. PATENT DOCUMENTS 5,089,274  2/1992  Marra et al. ............................ 424/534
5,198,541  3/1993  Elsbach .

OTHER PUBLICATIONS

Tobias et al., *J. Biol. Chem.*, 263:13479–13481, 1988.
Marra et al., *J. Immunol.*, 144:662–666, 1990.
Weiss et al., *Blood*, 69:652–659, 1987.
Mannion et al., *J. Immunol.*, 142:2807–2812, 1989.
Gray et al., *J. Biol. Chem.*, 264:9505–9509, 1989.
Tobias et al., *J. Biol. Chem.*, 264:10867–10871, 1989.
Veld et al., *Infection and Immunity*, 56:1203–1208, 1988.
Elsbach, *Trends in Biotechnology*, 8:26–30, 1990.
Weiss et al., *Infection and Immunity*, 51:594–599, 1986.
Farley et al., *Infection and Immunity*, 56:1589–1592, 1988.
Weiss et al., *J. Clin. Invest.*, 65:619–628, 1980.
Weiss et al., *Infection and Immunity*, 38:1149–1153, 1982.
Weiss et al., *J. of Immunol.*, 132:3109–3115, 1984.
Weiss et al., *J. Clin. Invest.*, 71:540–549, 1983.
Weiss et al. J. Biol. Chem. vol. 253 No. 8 (1978).
Ooi et al. J. Biol. Chem. vol 262 No. 31 (Nov. 5, 1987) 14891–14894.
Weiss et al. (Abstract, The American Federation for Clinical Research May 2, 3, 4, & 5 1986).

*Primary Examiner*—Jill Warden
*Assistant Examiner*—David Lukton
*Attorney, Agent, or Firm*—Marshall, O'Toole, Gerstein, Murray & Borun

[57] ABSTRACT

Disclosed herein are methods of inhibiting the endotoxin-mediated release of cytokines in a mammal by administering a 30 kD C-terminal fragment of bactericidal/permeability-increasing protein. The disclosed fragments are useful to treat mammals suffering from infections caused by gram-negative bacteria.

2 Claims, 13 Drawing Sheets

Bocterial Viabiliti

14C-Amino Acid Incorp.
(-Actinomycin D)

Phospholipid Hydrolysis

14C-Amino Acid Incorp.
(+Actinomycin D)

FIG. 5A

```
                                         -30
                                     met arg glu asn met ala arg gly pro cys asn ala
  1 CAGGGCCTTGAGGTTTTGGCAGCTCTGGAGG    ATG AGA GAG AAC ATG GCC AGG GGC CCT TGC AAC GCG
                               -20
          -20                                         -10                              1
    pro arg trp val ser leu met val leu val ala ile gly thr ala val thr ala ala val
 67 CCG AGA TGG GTG TCC CTG ATG GTG CTC GTC GCC ATA GGC ACC GCC GTG ACA GCG GCC GTC
                                         10                               20
    Asn Pro Gly Val Val Val Arg Ile Ser Gln Lys Gly Leu Asp Tyr Ala Ser Gln Gly
127 AAC CCT GGC GTC GTG GTC AGG ATC TCC CAG AAG GGC CTG GAC TAC GCC AGC CAG GGG
                               30                               40
    Thr Ala Ala Leu Gln Lys Glu Leu Lys Arg Ile Lys Ile Pro Asp Tyr Ser Asp Ser Phe
187 ACG GCT GCT CTG CAG AAG GAG CTG AAG AGG ATC AAG ATT CCT GAC TAC TCA GAC AGC TTT
                                         50                               60
    Lys Ile Lys His Leu Gly Lys Gly His Tyr Ser Phe Tyr Ser Met Asp Ile Arg Glu Phe
247 AAG ATC AAG CAT CTT GGG AAG GGG CAT TAT AGC TTC TAC AGC ATG GAC ATC CGT GAA TTC
                               70                               80
    Gln Leu Pro Ser Ser Gln Ile Ser Ala Gln Leu Gln Lys Phe Ser Ile Ser
307 CAG CTT CCC AGT TCC CAG ATA AGC                                          ATC AGC
                                         90                              100
    Asn Ala Asn Ile Lys Ile Ser Gly Lys Trp Lys Ala Gln Lys Arg Phe Leu Lys Met Ser
367 AAC GCC AAT ATC AAG ATC AGC GGG AAA TGG AAG GCA CAA AAG AGA TTC TTA AAA ATG AGC
                               110                              120
    Gly Asn Phe Asp Leu Ser Ile Glu Gly Met Ser Ile Ser Ala Asp Leu Lys Leu Gly Ser
427 GGC AAT TTT GAC CTG AGC ATA GAA GGC ATG TCC ATT TCG GCT GAT CTG AAG CTG GGC AGT
```

FIG. 5B

```
      Asn Pro Thr Ser Gly Lys Pro Thr Ile Thr Cys Ser Ser Cys Ser Ser His Ile Asn Ser
                                     130                               140
487   AAC CCC ACG TCA GGC AAG CCC ACC ATC ACC TGC TCC AGC AGC TGC AGC ATC AAC AGT

Val His Val His Ile Ser Lys Ser Lys Val Gly Trp Leu Ile Gln Leu Phe His Lys Lys
                          150                                          160
547   GTC CAC GTG CAC ATC TCA AAG AGC AAA GTC GGG TGG CTG ATC CAA CTC TTC CAC AAA AAA

Ile Glu Ser Ala Leu Arg Asn Lys Met Asn Ser Gln Val Cys Glu Lys Val Thr Asn Ser
                              170                                      180
607   ATT GAG TCT GCG CTT CGA AAC AAG ATG AAC AGC CAG GTC TGC GAG AAA GTG ACC AAT TCT

Val Ser Ser Lys Leu Gln Pro Tyr Phe Gln Thr Leu Pro Val Met Thr Lys Ile Asp Ser
                                  190                                  200
667   GTA TCC TCC AAG CTG CAA CCT TAT TTC CAG ACT CTG CCA GTA ATG ACC AAA ATA GAT TCT

Val Ala Gly Ile Asn Tyr Gly Leu Val Ala Pro Pro Ala Thr Thr Ala Glu Thr Leu Asp
                                      210                              220
727   GTG GCT GGA ATC AAC TAT GGT CTG GTG GCA CCT CCA GCA ACC ACG GCT GAG ACC CTG GAT

Val Gln Met Lys Gly Glu Phe Tyr Ser Glu Asn His His Asn Pro Pro Phe Ala Pro
                                          230                          240
787   GTA CAG ATG AAG GGG GAG TTT TAC AGT GAG AAC CAC CAC AAT CCA CCT TTT GCT CCA

Pro Val Met Glu Phe Pro Ala Ala His Asp Arg Met Val Tyr Leu Gly Leu Ser Asp Tyr
                                              250                          260
847   CCA GTG ATG GAG TTT CCC GCT GCC CAT GAC CGC ATG GTA TAC CTG GGC CTC TCA GAC TAC

Phe Phe Asn Thr Ala Gly Leu Val Tyr Gln Glu Ala Gly Val Leu Lys Met Thr Leu Arg
                                                  270                            280
907   TTC A C ACA GCC GGG CTT GTA TAC CAA GAG GCT GGG GTC TTG AAG ATG ACC CTT AGA
```

FIG. 5C

```
                        290                         300
     Asp Asp Met Ile Pro Lys Glu Ser Lys Phe Arg Leu Thr Thr Lys Phe Phe Gly Thr Phe
 967 GAT GAC ATG ATT CCA AAG GAG TCC AAA TTT CGA CTG ACA ACC AAG TTC TTT GGA ACC TTC
                        310                         320
     Leu Pro Glu Val Ala Lys Lys Phe Pro Asn Met Lys Ile Gln Ile His Val Ser Ala Ser
1027 CTA CCT GAG GTG GCC AAG AAG TTT CCC AAC ATG AAG ATA CAG ATC CAT GTC TCA GCC TCC
                        330                         340
     Thr Pro Pro His Leu Ser Val Gln Pro Thr Gly Leu Thr Phe Tyr Pro Ala Val Asp Val
1087 ACC CCG CCA CAC CTG TCT GTG CAG CCC ACC GGC CTT ACC TTC TAC CCT GCC GTG GAT GTC
                        350                         360
     Gln Ala Phe Ala Val Leu Pro Asn Ser Ser Leu Ala Ser Leu Phe Leu Ile Gly Met His
1147 CAG GCC TTT GCC GTC CTC CCC AAC TCC TCC CTG GCT TCC CTC TTC CTG ATT GGC ATG CAC
                        370                         380
     Thr Thr Gly Ser Met Glu Val Ser Ala Glu Ser Asn Arg Leu Val Gly Glu Leu Lys Leu
1207 ACA ACT GGT TCC ATG GAG GTC AGC GCC GAG TCC AAC AGG CTT GTT GGA GAG CTC AAG CTG
                        390                         400
     Asp Arg Leu Leu Leu Glu Leu Lys His Ser Asn Ile Gly Pro Phe Pro Val Glu Leu Leu
1267 GAT AGG CTG CTC CTG GAA CTG AAG CAC TCA AAT ATT GGC CCC TTC CCG GTT GAA TTG CTG
                        410                         420
     Gln Asp Ile Met Asn Tyr Ile Val Pro Ile Leu Val Leu Pro Arg Val Asn Glu Lys Leu
1327 CAG GAT ATC ATG AAC TAC ATT GTA CCC ATT CTT GTG CTG CCC AGG GTT AAC GAG AAA CTA
                        430                         440
     Gln Lys Gly Phe Pro Leu Pro Thr Pro Ala Arg Val Gln Leu Tyr Asn Val Val Leu Gln
1387 CAG AAA GGC TTC CCT CTC CCG ACG CCG GCC AGA GTC CAG CTC TAC AAC GTA GTG CTT CAG
```

```
              Pro His Gln Asn Phe Leu Leu Phe Gly Ala Asp Val Val Tyr Lys
                                        450
1447 CCT CAC CAG AAC TTC CTG CTG TTC GGT GCA GAC GTT GTC TAT AAA TGA AGGCACCAGGGG

1507 TGCCGGGGGCTGTCAGCCCGCCACCTGTCCTGATGGGCCTGTGGGCACCGGCTGCCTTTCCCCAGGGAATCCTCTCCAG

1585 ATCTTAACCAAGAGCCCCCTTGCAAACTTCTTTCGACTCAGATTCAGAAATGATCTAAACACGAGGAAACATTATTCATT

1663 GGAAAAAGTGCATGGTGTGTATTTTAGGGATTATGAGCTTCTTTCAAGGGCTAAGGCTGCAGAGATATTTCCTCCAGGA

1741 ATCGTGTTTCAATTGTAACCAAGAAATTTCCATTTGTGCTTCATGAAAAAAACTTCTGGTTTTTTCATGTG--- poly-A tail
```

FIG. 5D

—O— Holo-BPI
—▲— 25 kDa fragment
—□— 30 kDa fragment

BIOLOGICALLY ACTIVE BACTERICIDAL/PERMEABILITY-INCREASING PROTEIN FRAGMENTS

The United States government has rights to this invention by virtue of research grant Nos. R37DK-05472 and A1-18571 from the National Institutes of Health.

This application is a continuation of application Ser. No. 07/754,204, filed Aug. 26, 1991, now abandoned, which is in turn a continuation-in-part of Ser. No. 07/621,473, filed Dec. 3, 1990, now abandoned, which is in turn a continuation-in-part of Ser. No. 07/228,035, filed Aug. 5, 1988, now abandoned, which is in turn a continuation-in-part of Ser. No. 07/084,335, filed Aug. 11, 1987, now abandoned.

BACKGROUND OF THE INVENTION

The present invention pertains to biologically active, polypeptide fragments of mammalian bactericidal/permeability-increasing proteins and to methods for making and using said fragments.

Bactericidal/permeability-increasing protein (BPI) is a 50 to 60 Kd protein, isolated from the granules of mammalian polymorphonuclear leukocytes (PMN) which are blood cells that are essential in the defense against invading microorganisms in mammals. BPI occurs only in cells of the myeloid series of blood cells, is produced at the promyelocytic/myelocytic stage of differentiation and is located in the primary granules in these cells.

BPI is a potent cytotoxin (and therefore bactericidal agent) active against a broad range of gram negative bacterial species. BPI also inhibits endotoxin activity by neutralizing gram negative bacterial lipopolysaccharides (LPS). It exhibits a high degree of specificity in its cytotoxic effect: for example, 10–40 nM (0.5–2.0 micrograms) kill more than 90% of $10^7$ sensitive bacteria whereas 100-fold higher concentrations of BPI are non-toxic for other microorganisms and eukaryotic cells. All available evidence suggests that in the intact PMN and in chide leukocyte fractions, BPI is the principal oxygen-independent agent that is active against BPI-sensitive bacteria. Furthermore, its anti-LPS activity makes BPI a very good candidate for down-regulating responses triggered by LPS not only by halting bacterial proliferation but also by directly inhibiting the effects of released LPS. Endotoxins, i.e., complex lipopolysaccharides (LPS) are the major components of the outer envelope of gram negative bacteria, and account primarily for the most serious clinical consequences of gram negative bacterial infections. Young, L. S. in: Principles of Infectious Diseases (1990), Mandell, G. L., Douglas, R. D., and Bennett, J. E., eds., Churchill-Livingstone, New York, pp. 611–635. As little as subnanogram-to-ng/ml concentrations of these agents elicit in the host many cellular and extracellular responses, including the production and release of a diverse network of mediators such as activated Complement components, cytokines (e.g., tumor necrosis factor, interleukins), arachidonate metabolites, etc. Morrison, D. C. and Ryan, J. L. (1987) *Ann. Rev. Med.,* 38:417–432. While these reactions must have evolved as part of essential host defenses, they may also become excessive and self-destructive. Young, (1990), supra; Morrison, (1987), supra; Beutler, B. and Cerami, A. (1986) *Nature,* 320:584–588, prompting many investigators to attempt to attenuate host responses to LPS. Recent reports indicate life-saving effects of monoclonal antibodies, directed against the biologically active lipid A portion of the LPS molecule, in Patients with gram negative bacteremia and sepsis. Ziegler, E., Fisher, C., Sprung, C., Straube, R., and Sadoff, J. (1990) *Clin. Res.,* 38:304A, in accord with a primary role of endotoxin in the pathogenesis of gram negative sepsis and supporting the potential clinical usefulness of anti-LPS directed therapies.

Progress has also been made in the identification and characterization of endogenous LPS-binding proteins, produced by various cells and tissues. Ulevitch, R. J., Johnston, A. R., and Weinstein, D. B. (1981) *J. Clin. Invest.,* 67:827–837; Munford, R. S., Andersen, J. M., and Dietschy, J. M. (1981) *J. Clin. Invest.,* 68:1503–1513; Munford, R. S., and Hall, C. L. (1986) *Science,* 234:203–205; Tobias, P. S., Soldau, K., and Ulevitch, R. J. (1986) *J. Exp. Med.,* 164:777–793; Roeder, D. J., Lei, M., and Morrison, D. C. (1989) *Infect. and Immun.,* 57: 1054–1058, that may mediate and regulate the host's response to LPS. Among these proteins is a LPS-binding protein (LBP) that is produced and secreted by the liver and accumulates in plasma at least one hundred-fold higher than normal concentrations during the acute phase response that is triggered by LPS and many other irritants. Tobias, (1986), supra. In vitro LBP enhances the delivery of LPS and LPS-containing cells to macrophages and magnifies responses of macrophages and polymorphonuclear leukocytes (PMN) to LPS (Wright, S. D., Tobias, P. S., Ulevitch, R. J., and Ramos, R. A. (1989) *J. Exp. Med.,* 170:1231–1241; Vosbeck, K., Tobias, P. S., Mueller, H., Allen, R. A., Arfors, K., Ulevitch, R. J., and Sklar L. A. (1990) *J. Leuk. Biol.,* 47:97–104), suggesting that the function of LBP is to heighten the host's response to LPS. In contrast, a related LPS-binding protein present in PMN, the bactericidal/permeability-increasing protein (BPI; Tobias, P. S., Mathison, L. C., and Ulevitch, R. J. (1988) *J. Biol. Chem.,* 263: 13479–13481 ), suppresses both endotoxin-mediated activation of procoagulant protease(s) in Limulus amebocyte lysates and upregulation of CR1 and CR3 receptors on the surface of PMN (Marra, M. N., Wilde, C. G., Griffith, J. E., Snable, J. L., and Scott, R. W. (1990) *J. Immunol.,* 144:662–666).

BPI isolated from both human and rabbit PMN has been purified to homogeneity. The molecular, weight of human BPI is approximately 58,000 Daltons (58 kDa) and that of rabbit BPI is approximately 50 kDa. The amino acid composition of these two proteins is closely similar as is the amino acid sequence of their $NH_2$-terminal amino acid residues. Both proteins are highly basic, having an isoelectric point greater than 9.6.

The anti-microbial effects of BPI require attachment of the protein to the surface of the susceptible gram negative bacteria. Initial binding of BPI to target cells involves electrostatic interactions between the basic protein and the negatively charged sites on the lipopolysaccharides (LPS) on the properties of the bacterial outer membrane and leads to discrete alteration in the permeability properties of the bacterial membrane and activation of enzymes that degrade phospholipids and peptidoglycans. The final stage of action is the actual killing of the bacteria by an as yet unknown mechanism that involves damage to structural and functional elements associated with the cytoplasmic membrane. The closely similar amino acid composition and nearly identical bactericidal and membrane-perturbing properties of BPI purified from human and rabbit PMN suggest that this protein has been highly conserved during evolution and is an important member of the anti-bacterial arsenal of the mammalian PMN.

Due to its potent bactericidal action against gram negative bacteria and lack of cytotoxicity towards other microorganisms and eukaryotic cells, it is envisioned that BPI may be employed as a chemotherapeutic agent and/or as a model for the design of new antibiotic agents. The possibility has been raised that, as in the case with other cytotoxic proteins, the different functions of BPI, namely binding, envelope-altering and killing reside in different domains within the BPI molecule. Although BPI fragments, obtained by digestion of the holoproteins with the proteolytic enzyme elastase, have been reported (Weiss, J. et al., *Clin. Res.*, 34:537A, 1986), the fragments tested remained associated under the nondenaturing conditions employed. No biological activity was ascribed to any isolated fragments. Moreover, antibodies directed against the holoprotein did not recognize these fragments under denaturing condition when analyzed using the well-known Western blotting procedure.

Therefore, in light of the above, there is a need in the art for biologically active peptide fragments of BPI for use as bactericidal/permeability increasing agents as well as therapeutic (e.g., antibacterial and antiendotoxin) agents. Such BPI fragments are also needed to provide structural information to direct the design of future generations of novel antimicrobial agents specific against gram negative bacteria and to be used as probes into the molecular organization of the multifunctional holo-BPI protein.

OBJECTS OF THE INVENTION

It is an object of the present invention to provide biologically active peptide fragments of mammalian BPI.

Another object of the present invention is to provide biologically active peptide fragments of mammalian BPI with improved antimicrobial and/or antiendotoxin effectiveness.

Yet another object of the present invention is to provide a process for the production of biologically active peptide fragments of mammalian BPI.

Yet another object of the present invention is to provide methods for treating mammals suffering from infections caused by gram negative bacteria, and/or from one or more clinical consequences of such infections (e.g., septic shock).

A further object of the present invention is to provide a method for increasing the permeability of gram negative bacteria.

A still further object of the present invention is to increase the effectiveness of gram negative bactericidal agents.

These and other objects of the present invention will be apparent to those of ordinary skill in the art in light of the present description, accompanying claims and appended drawings.

SUMMARY OF THE INVENTION

The present inventors have unexpectedly discovered biologically active fragments of mammalian BPI substantially shorter in length than the native BPI protein. Although these fragments are substantially smaller than the native molecule, they retain at least substantially all of the bactericidal and permeability-increasing properties of the intact protein as well as substantially all of its anti-LPS (or antiendotoxin) properties.

The biologically active BPI fragments of the present invention can be produced by incubating a sample comprising the BPI holoprotein under BPI cleaving conditions and recovering biologically active fragments of the BPI holoprotein. The preferred BPI cleaving conditions include heating of the BPI holoprotein in an acceptable buffer for a time ranging between about 16 and 24 hours at a temperature between about 20° C. and about 37° C.

In another aspect, the present invention provides a method for treating mammals suffering from infections caused by gram negative bacteria comprising administering to mammals in need of such treatment a gram negative bactericidal-effective (and/or antiendotoxin) amount of at least one of the above-mentioned biologically active BPI fragments or pharmaceutically acceptable salts thereof.

In another aspect, the present invention provides pharmaceutical formulations for treating infections in mammals caused by gram negative bacteria (or for treating one or more endotoxin-associated clinical consequences of such infections) comprising a gram negative bactericidal-effective amount (or endotoxin-inhibitive effective amount) of at least one of the biologically active BPI fragments or pharmaceutically-acceptable salts thereof.

In yet another aspect, the present invention provides a method for increasing the permeability of gram negative bacteria comprising incubating the bacteria with a gram-negative-bacterial-permeability-increasing-effective amount of a biologically active fragment of BPI.

In still another aspect, the present invention provides a method for increasing the effectiveness of gram negative bactericidal agents in mammals in need of such treatment, comprising co-administration of one or more of such agents with the biologically active fragments of BPI.

A still further aspect of the present invention is directed to a purified, isolated DNA sequence having the sequence set out in FIG. 5 or its complementary strand and DNA sequences hybridizing under stringent hybridization conditions with said DNA sequences. Such DNA sequences encode the human bactericidal/permeability-increasing protein and fragments thereof including biologically active peptides having substantially the same activity as BPI.

BRIEF DESCRIPTION OF THE DRAWINGS

FIGS. 5A, 5B, 5C, and 5D, bottom line, shows the sequence of the cDNA encoding human BPI whereas printed above is the corresponding amino acid sequence. The two potential glycosylation sites are overlined.

DETAILED DESCRIPTION OF THE INVENTION

Figure 1:
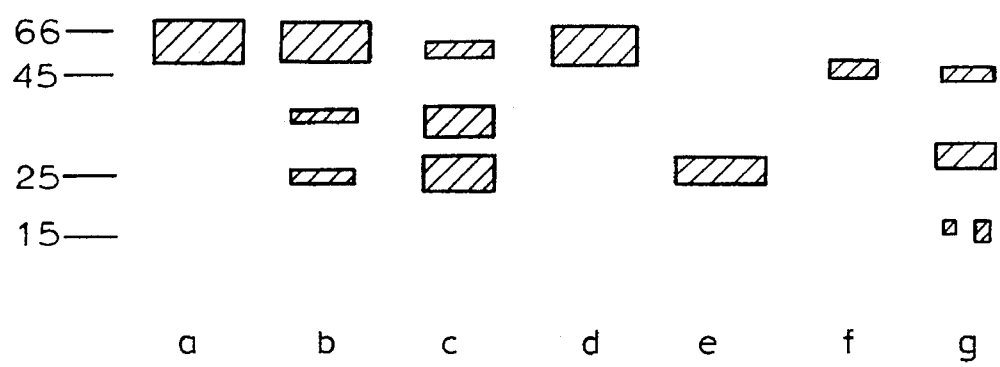
FIG. 1 is a photograph of a stained SDS-PAGE gel showing the production and purification of the human BPI fragment of a preferred embodiment of the present invention.

All references and patent applications cited herein are incorporated by reference in their entirety.

The present inventors have unexpectedly discovered biologically active fragments of BPI isolated from mammalian PMN. $NH_2$-terminal amino acid sequence analysis demonstrated that, in the case of human BPI, such fragments represent a portion of the BPI molecule derived from the $NH_2$-terminus, as shown in Example 3 below. These fragments exhibit essentially all of the antibacterial and membrane permeability-increasing functions contained in the complete molecule (as well as the LPS-neutralizing function) but are substantially smaller (i.e., have a lower molecular weight) than the holoprotein. "Substantially smaller" is defined herein as being up to about half the size of the holoprotein. This is an unexpected finding because, in the case of other cytotoxins such as diphtheria toxin, cholera toxin and ricin (toxins which do not demonstrate the unique specificity of the BPI holoprotein), studies have revealed that individual functions, such as binding or catalytic activity, can be expressed by isolated fragments, but that cytotoxicity (comprising both binding to a cell membrane and intracellular toxic activity) requires essentially the entire molecule.

In addition, the present inventors have discovered that the N-terminal fragments as well as C-terminal fragment(s) of human BPI are capable of inhibiting the production and/or release of Tumor Necrosis Factor (TNF) triggered by LPS in whole blood. This is a surprising and unexpected finding in that previously no bactericidal and little or no LPS neutralizing activities had been ascribed to the approximately 30 kD C-terminal human BPI fragment. Thus the C-terminal fragment is suitable for administration to mammals suffering from diseases mediated by bacterial endotoxin or LPS.

The BPI fragments of the present invention are as potent bactericidal agents as the holoprotein against rough *E. coli*, more potent than the holoprotein against the generally more resistant, smooth *E. coli* (on a molar basis), and retain the specificity of the holoprotein towards gram negative bacteria. This is a particularly important finding because smooth gram negative bacteria (smoothness being due to the presence of longer polysaccharide chains in the bacterial cell envelope) generally are more pathogenic than their corresponding rough counterparts.

In addition, the BPI fragments of the present invention also possess the molecular determinants for most if not all the LPS-recognition and LPS-neutralization of the holoprotein. Thus, in experiments described below with LPS from both rough and smooth *E. coli* and *S. typhimurium* the amino terminal fragment accounted for nearly all activity of the holoprotein.

The size, chromatographic behavior (FIGS. 1 and 2 below) amino acid content (Table 1 below) and partial sequence (see Example 4 below) establish that the BPI fragment of the present invention is a distinct molecular entity derived from the N-terminal half of the holoprotein. The same fragment possesses substantially all of the anti-LPS activity.

Non-limiting examples of the BPI fragments of the present invention are approximately 25 kDa for human and rabbit BPI. The human 25 kDa fragment of the preferred embodiment of the present invention was initially isolated after long-term storage (e.g., two months) of the purified holoprotein in a weakly acidic buffer (10 mM ammonium acetate, pH 4.6) and can be thus generated. However, it is preferable to produce the BPI fragments of the present invention by incubating the holoproteins in an acceptable buffer i.e., a buffer having sufficient buffering capacity at concentrations between about 10 and about 150 mM at a pH ranging between about 6.0 and about 8.0, such as Tris/HCl, phosphate, and preferably HEPES/NaOH (Sigma Chemicals, St. Louis, Mo.), or mixtures thereof. The preferred pH is 7.4. The incubations may be performed for a period of time broadly ranging between about 16 and 24 hours and preferably 18 hours, at a temperature ranging between about 20° C. and about 37° C. and preferably 37° C. A particularly preferred condition comprises incubation in 0.1M HEPES/NaOH buffer, pH 7.4 for 18 hours at 37° C. This has led to the conversion of about 50% of the holoprotein into the biologically active fragments of the present invention. Reincubation of the recovered holoprotein, under these conditions again results in formation of the 25 kDa fragment.

The 25 kD N-terminal fragment can be dried and resuspended.

The 25 kD N-terminal fragment of human BPI results from cleavage of the holoprotein between residues 199–200 and 203–204 during the limited proteolysis of BPI. The remaining approximately 30 kD fragment of BPI possesses no detectable amount (less than about 5%) of the antibacterial activity and only about 10% of the anti-LPS activity of the holoprotein.

The BPI holoproteins, used as starting materials for the production of the biologically active fragments of the present invention, can be obtained from mammalian cells of the myeloid series of blood cells, such as PMN. Although the fragments of the present invention are not limited to a particular mammalian species, it is preferable to employ such fragments isolated from a homologous mammalian species when treating mammals afflicted with bacterial infections caused by gram negative bacteria or endotoxin-associated clinical consequences of such infections.

In addition, the BPI holoprotein and/or the biologically active fragments of the present invention may be obtained using recombinant DNA techniques employing the sequence information presented below in Example 3 to synthesize DNA probes for the detection of DNA sequences coding for BPI in complementary DNA or genomic libraries using methods well-known in the art. The gene coding for the BPI holoprotein, or a portion of the gene coding for the 25 kDa fragment of the present invention (and possibly smaller biologically active fragments thereof) may be inserted into a suitable expression vector for the production of biologically active polypeptides.

In one embodiment, human BPI holoprotein can be obtained from PMN isolated from normal blood or from blood from patients with chronic myelocytic leukemia, as detailed in Example 1 below. Alternatively, human BPI can be extracted from the human leukemic cell line HL-60 (available as ATCC CCL 240, American Type Culture Collection, Rockville, Md.). The latter have been found to contain approximately 10 micrograms of BPI holoprotein per $10^8$ cells. Mature PMN of either normal or leukemic origin contain approximately 60 micrograms per $10^8$ cells of the BPI holoprotein and are therefore the preferred starting material.

Once obtained, the mammalian PMN can be fractionated using, for example, the procedures detailed below in Examples 1 or 6 in order to obtain primary granules (or alternatively by extraction of whole cells with 0.16N sulfuric acid, as described in Elsbach, P. et al., *J. Biol. Chem.*, 254:11000, 1979). Such primary granules isolated from PMN or leukemic cell lines contain the bulk of BPI holoprotein activity (see Weiss et al., *Blood*, 69:652–659, 1987). The BPI holoprotein can then be extracted and purified using any technique known in the art which yields a biologically active BPI holoprotein, including the "affinity" purification procedure as described by Mannion et al., *J. Immunol.*, 142:2807–2812, 1989. Although crude extracts obtained from such primary granules can be employed as starting materials for the production of the BPI fragments of the present invention, it is preferable to purify the holoprotein before generating the fragments. Preferred extraction and purification techniques for human and rabbit BPI holoproteins are described in Examples 1 and 6 below.

The amounts of starting, purified, BPI holoprotein to be employed in practicing the present invention preferably should be at least 200 micrograms of purified holoprotein. Although it is possible to use smaller amounts of material, this may hamper the recovery of the biologically active fragments due to non-specific losses, as is true with many other biologically-active proteins, such as interferons.

Although not wishing to be bound by any theory of operation of the present invention, it is believed that the cleavage of the holoprotein to generate the biologically active fragments of the present invention is due to the presence of serine proteases. The cleavage sites have been identified above.

The protein cleaving conditions necessary for the production of the biologically active BPI fragments of the present invention are broadly within the pH, temperature and time optima of such serine proteases, i.e., pH 6.0–pH 8.0, 20° C.–37° C., 16–24 hours. Such incubation of the BPI holoprotein will produce cleavage at about 25 kDa from the $NH_2$-terminus of the holoprotein. See Examples 2 and 6.

The biologically active BPI fragments of the present invention can be utilized for the treatment of mammals suffering from diseases caused by gram negative bacteria, such as bacteremia or sepsis. Due to their exquisite selectivity and lack of cytotoxicity toward cells other than gram negative bacteria, the BPI fragments of the present invention would be particularly useful as specific therapeutic agents. Currently gram negative bacterial infections, such as those caused by *Escherichia coli*, various species of Salmonella, Klebsiella or Pseudomonas are treated with antibiotics, such as penicillin derivatives, aminoglycosides and chloramphenicol. The effectiveness of antibiotics is limited due to the fact that gram negative bacilli tend to display significant intrinsic resistance to many currently available antibiotics and to readily develop further resistance due to the acquisition of resistance factor plasmids. Under appropriate selective conditions, rapid dissemination of multiple antibiotic resistance among a wide variety of gram negative pathogens is known to occur. Moreover, antibodies that are available to treat gram negative bacteremia may often cause shedding of bacterial endotoxin during bacterial killing and consequently exacerbation of clinical problems. Recently monoclonal, anti-LPS IgM antibodies have been prepared commercially and have been used in animal models and in clinical trials for treatment of bacteremia and septic shock with apparent improvement in survival—(*Fed. Proc.*, 38:304A, 1990). Since the effect of the monoclonal antibodies on mortality was modest, the need is evident for additional or more effective agents that can be used alone or in combination with the anti-LPS antibodies. The combined antibacterial and the endotoxin neutralizing activities of the BPI fragments in vitro raise the possibility that these molecules may serve as such therapeutic agents.

When employed to treat bacteremia (i.e., the presence of bacteria in the blood stream) or sepsis (bacterial contamination of bodily fluids) or septic shock due to LPS caused by gram negative bacteria in a mammal, the BPI fragments of the present invention are preferably administered parenterally, and most preferably intravenously in amounts broadly ranging between about 1 microgram and 1000 micrograms per kg body weight of said mammal and preferably between about 10 micrograms and about 250 micrograms per kg body weight per treatment. The duration and number of treatments may vary from individual to individual, depending upon the severity of the illness. A typical treatment regime may comprise intravenous administration of about 100–200 micrograms per kg body weight of the BPI fragments three times a day. To help avoid rapid clearance of the BPI fragments of the present invention (and indeed the holoproteins) the BPI fragments may be coupled with physiologically-acceptable carriers, such as normally occurring serum proteins (e.g., albumin or lysozyme). The BPI fragments of the present invention could also be employed topically to treat mammals suffering from skin infections caused by susceptible gram negative bacteria which occur in bedridden patients suffering from decubitus ulcers (bed sores) or in burn patients. When employed as a topical antibacterial agent, the BPI fragments may be administered in the same dosages and frequency as described for parenteral administration above, i.e., 100–200 micrograms/ kg body weight.

When employing the approximately 30 kD BPI C-terminal fragment(s) for treating a mammal suffering from the deleterious effects of LPS, the anti-endotoxin and anti-Tumor Necrosis Factor releasing effective amounts would be the same as disclosed above for the N-terminal fragment, i.e., broadly ranging between about 1 microgram per kg body weight of said mammal and 1000 micrograms per kg body weight of said mammal and preferably between about 10 micrograms per kg body weight of said mammal and 250 micrograms per kg body weight of said mammal. Either of the 30 kD C-terminal fragments disclosed below may be used separately or as a mixture. The same frequencies and routes of administration and carriers and diluents mentioned above may be employed in this embodiment of the present invention.

In addition, the BPI polypeptides of the present invention may be administered, in effective amounts and frequencies as described above, to treat individuals who are at an increased risk of contracting an infection caused by a gram negative bacterium (and therefore at an increased risk for an LPS-mediated disease). Such patients include immunosuppressed individuals, such as those undergoing chemotherapy to treat a malignancy (such as cancer) and individuals who are immunosuppressed due to infection by human immunodeficiency virus (HIV) and/or are suffering from Acquired Immunodeficiency Syndrome (AIDS).

The BPI N- and C-terminal fragments of the present invention can be incorporated in pharmaceutical formulations to be used to treat mammals suffering from gram negative bacterial infections. Pharmaceutical formulations comprising the BPI fragments of the present invention (or physiologically-acceptable salts thereof) as at least one of the active ingredients, would in addition optionally comprise pharmaceutically-acceptable carriers, diluents, fillers, salts and other materials well-known in the art depending upon the dosage form utilized. For example, preferred parenteral dosage forms would comprise a sterile isotonic saline solution, and may comprise between about 1 microgram and 1000 micrograms of one or more BPI fragments of the present invention, alternatively covalently coupled to suitable physiologically-acceptable carriers, such as normally occurring serum proteins, for example lysozyme or albumin, if needed to retard their clearance. For use in treating mammals with gram negative bacterial infections in body fluids largely devoid of (lipo) proteins, such as urine, pharmaceutical formulations may for example comprise the above amounts of BPI fragments of the present invention and sterile, isotonic saline solutions for irrigation of the urinary tract.

In another preferred embodiment, the BPI fragments of the present invention in amounts ranging between 1 microgram and 1000 micrograms per dose, may be mixed with antibiotics and may be formulated in the same type of preparations used in antibiotic creams (such as Silvadene, Marion Laboratories, Kansas City, Mo., Terramycin, Pfipharmecs, New York, N.Y. or Achromycin, Lederle Laboratories, Pearle River, N.Y.) well-known in the art for topical administration.

In another preferred embodiment of the present invention, pharmaceutical formulations for treating mammals suffering from gram negative bacterial infections may contain the BPI fragments of the present invention in addition to standard amounts (well-known in the art) of antibiotics such as Penicillin-G (available from E. R. Squibb and Sons, Inc., Princeton, N.J.) or cephalosporins (available from Eli Lily & Co., Indianapolis, Ind.). In a particularly preferred embodiment, the BPI fragments of the present invention may be mixed with hydrophobic antibiotics, such as rifampicin (available as RIFAMPIN, CIBA Pharmaceutical CO., Summit, N.J.), and hydrophobic penicillins such as Penicillin-V Benzathine (Lederle Labs, Pearl River, N.Y.). The increased permeability of gram negative bacteria after treatment with BPI or the N-terminal fragments is expected to enhance the effectiveness of such antibiotics which cannot easily enter non-permeabilized bacteria.

In yet another preferred embodiment, use of the BPI fragments can be combined with use of 15 kD mammalian polypeptides which have been found to potentiate both the anti-LPS and the anti-bacterial activity of BPI (see copending commonly assigned U.S. patent application Ser. No. 502,560 filed Mar. 30, 1990).

Because of the increased sensitivity to the fragments of the present invention of the more pathogenic, smooth, gram negative bacteria, the BPI fragments of the present invention are expected to decrease resistance of such bacteria to the above-described antibiotics. Substantially simultaneous administration of the fragments of the present invention and the antibiotic or other co-treating agent of choice is preferred.

An example of the above-mentioned embodiment is demonstrated in Example 4 below, wherein actinomycin D (which normally cannot enter and affect gram negative bacteria due to its hydrophobic properties) significantly inhibited RNA and protein synthesis only in BPI-treated *E. coli*.

It will be appreciated that the unit content of active ingredients contained in an individual dose of each dosage form or composition need not in itself constitute an effective amount for killing or inhibiting the growth of or the LPS-associated clinical consequences of gram negative bacterial infections since the necessary effective amount in each case can be reached by administration of a plurality of dosage forms and/or administrations (e.g., inclusion in the same dosage forms) of additional active ingredients such as those described above (whether the combined effects of such ingredients and the active BPI fragments of the present invention are additive or synergistic).

In addition, the present inventors have isolated the gene encoding the human BPI holoprotein and have identified and sequenced BPI cDNA isolated from human promyelocytic leukemia cells (HL-60). The nucleotide sequence of the cDNA and the corresponding amino acid sequence of the holoprotein are set forth in FIG. 5.

The sequence information contained in FIG. 5 can be employed to synthesize the 25 kDa, biologically active fragment of BPI. In this case, a vector can be generated comprising DNA residues 123 to about 759–780 (or amino acid residues 1 to about 210–220 or 1–199 or 1–203) of FIG. 5 (see, e.g., the amino acid and DNA sequences respectively set out in SEQ. ID NOS: 3 and 4) using techniques well-known in the art. In addition, smaller sub-fragments of the cDNA of FIG. 5 can be generated using, for example, limited Bal31 nuclease digestion of the entire cDNA, to probe for the minimum sequences necessary for BPI biological activities mentioned above.

Alternatively, the BPI holoprotein can be obtained after synthesis by suitably transfected or transformed eukaryotic (mammalian or yeast) or prokaryotic cells and the biologically-active 25 kDa fragments mentioned above can be obtained using the techniques described in Example 2 below.

The present invention is described further below in specific examples which are intended to illustrate it without limiting its scope.

EXAMPLE 1

ISOLATION AND PURIFICATION OF HUMAN BPI

Human leukocytes were obtained from heparin-treated venipuncture from healthy donors and patients with chronic myelocytic leukemia.

Populations of human PMN were obtained in two ways.

(1) PMN's were isolated by the dextran-sedimentation procedure, followed by centrifugation in an Isopaque-Ficoll gradient (Pharmacia Fine Chemicals, Piscataway, N.J.) as described (Boyum, A. J., *J. Clin. Lab. Invest. Suppl.*, 97:77–89, 1968). The leukocyte-rich plasma from healthy donors was first diluted with isotonic Krebs-ringer phosphate buffer (pH7.4) to a concentration of 10,000 to 20,000 cells/-microliter before layering on the Isopaque-Ficoll mixture. The cells were washed twice in Krebs-ringer phosphate before use.

(2) Alternatively, leukocyte-rich plasma obtained by leukopheresis (using procedures well-known in the art) of 400 ml of venous blood, from a patient with chronic myelocytic leukemia, was sedimented directly at 1000×g for five minutes yielding $3.5\times10^{10}$ leukocytes, essentially all of which were PMN. These cells were washed twice with Krebs-ringer phosphate before homogenization.

For extraction of the human BPI holoprotein, the PMN were first disrupted in one of two ways: 1) Granule-rich fractions, containing the bulk of the BPI activity, were obtained by homogenization at 0° C. of PMN suspended in 0.34M sucrose ($2\times10^8$ cells/ml), as described in Weiss, J. et al., *J. Biol. Chem.*, 253:2664–2672, 1978, followed by centrifugation at 400×g for 10 and 20,000×g for 30 minutes at 4° C. The granule rich pellet was extracted with approximately 10 volumes of 0.2M sodium acetate (pH 4.0), overnight at 4° C. with continuous stirring. The extract was collected as a supernatant by centrifugation of the extract at 20,000×g for 30 minutes.

2) Alternatively, PMN ($2-3\times10^8$ cells/ml) were disrupted in distilled water at 0° C. with a Potter-Elvejhem glass homogenizer and a motor-driven teflon pestle (Kontes; subsidiary of Kimble Div. of Owens, Ill.) and extracted at 0° C. for 30 minutes with 0.16N sulfuric acid to solubilize the BPI holoprotein. After centrifugation at 23,000×g for 20 minutes at 4° C. to sediment insoluble material, the extract was dialyzed against 200 mM sodium acetate/acetic acid buffer (pH 4.0). The BPI in these extracts was purified by gel filtration chromatography on a molecular sieving column (SEPHADEX G-75, superfine, Pharmacia Fine Chemicals, Piscataway, N.J.) at 4° C. The beads were prepared according to the manufacturer's instructions and equilibrated in the 0.2M sodium acetate (pH 4.0). Using this technique, substantially all of the BPI holoprotein activity was eluted as a single peak (fractions 35–39) corresponding to a discrete protein peak (5–6 % of the total protein applied) just after the void volume.

The chromatographic fraction containing the human BPI holoprotein was subjected to further chromatography on an ion exchange resin (SP-SEPHADEX, Pharmacia Fine Chemicals, Piscataway, N.J.). Protein was applied to the column, equilibrated in 0.1N NaCl-0.2M sodium acetate/acetic acid buffer (pH 4.6) and eluted with a stepwise gradient of buffered NaCl (0.3, 0.5 and 0.75M). Human BPI holoprotein eluted in the last step.

Purified human BPI holoprotein was then isolated by high performance liquid chromatography (HPLC) on a reversed phase C-4 (Vydac) column (Sota Chromatography, Crompand, N.Y.) using an HPLC system (Model 332, Beckman Instruments, Fullerton, Calif.). The column used a linear gradient of acetonitrile (0–95% volume/volume, J. T. Baker Chemical Co., Philipsburg, N.J.) in 0.1% trifluoroacetic acid (TFA, Pierce Chemical Co., Rockford, Ill.). Absorbance was monitored at 214 nm. Human BPI eluted at about 70% acetonitrile and was dialyzed against approximately 50 volumes of 10 mM ammonium acetate/acetic acid buffer (pH 4.6). Purified BPI was stored either in 0.15M sodium acetate/acetic acid buffer (pH 4.0) or in 10 mM ammonium acetate/acetic acid buffer (pH 4.0) at 4° C.

Alternatively, BPI can be purified rapidly, even from crude extracts of PMN-rich cell preparations by taking advantage of the preferential and reversible binding of BPI to target bacteria (e.g., *E. coli*, Mannion, B. A., Kalatzis, E. S., Weiss, J. and Elsbach, P., *J. Immunol.*, 142:2807–2812, 1989). Routinely, *E. coli*. J5 are used after growth of these bacteria to mid-late logarithmic phase in triethanolamine-buffered medium (Simon, E. J. and van Praag, D., *Proc. Natl. Acad. Sci. USA*, 51:877–883, 1964). After harvesting, the sedimented bacteria are resuspended with leukocyte extract (approx. $5-10\times10^8$ bacteria per ml of extract, representing 5–10 mg of total protein) and incubated at 37° C. for 10 min with gentle stirring. Incubations may be carried out in 10 mM acetate, or phosphate, or Tris-HCl or any other suitable buffer from pH 4.0 to pH 7.5 in the presence or absence or 0.9% (w/v) sodium chloride (Ooi, C. E., Weiss, J., Levy, O. and Elsbach, P., *J. Biol. Chem.*, 265:15956–15962, 1990)provided the proteins in the leukocyte extract remain fully soluble under these conditions. After the incubation the bacteria are sedimented (5000×g/10 min/4° C.) and washed twice with the same buffer to remove unbound protein. The bacteria containing bound protein are then resuspended in buffer supplemented with 200 mM $MgCl_2$ at $5\times10^9$ bacteria/ml, incubated at 37° C. for 15 min with shaking, and sedimented as described above. The recovered supernatant containing the previously bound protein, eluted by $Mg^{2+}$, is dialyzed against 1500 volumes of 20 mM sodium acetate/acetic acid buffer (pH 4.0) and stored at 4° C. The purity of the eluted protein is monitored by SDS-PAGE and, if necessary, an additional purification step is added consisting of reversed phase HPLC on a Vydac C4 column (The Separations Group, Hesperia, Calif.), using a linear gradient of acetonitrile (0–95%, v/v) in 0.1% (v/v) trifluoroacetic acid developed over 30 min at a flow rate of 1 ml/min.

EXAMPLE 2

PRODUCTION OF HUMAN BPI FRAGMENTS

Purified human BPI holoprotein was incubated in 0.1M HEPES-NaOH buffer, pH 7.4 for 18 hours, and then analyzed by sodium dodecylsulfate polyacrylamide gel electrophoresis (SDS-PAGE) in 12% polyacrylamide gels using the buffer system containing 0.375M Tris/HCl and 0.1% SDS of Laemmli, U.K., *Nature*, 227:680–685, 1970. The results are shown in FIG. 1. In FIG. 1, lanes A–E were stained using the well-known Coomassie blue technique and lanes F and G were silver stained using a commercial kit (Bio-Rad, Bio-Rad Labs, Richmond, Calif.).

Upon incubation in 10 mM ammonium acetate buffer (pH 4.6) at 4° C. for two months, 10 micrograms of the purified human protein (FIG. 1, lane A) fragmented into two species of approximately 30 and 25 kDa (FIG. 1, lane B). Incubation of purified human BPI holoprotein (10 micrograms) for 24 hours at 37° C. in 0.1M HEPES/NaoH buffer, pH 7.4, enhanced the accumulation of the two species, with the concomitant loss of the holoprotein (FIG. 1, lane C). Reversed phase HPLC of this incubated mixture, performed as described above for the holoprotein, yielded two major protein peaks, one co-eluting with native human BPI holoprotein and the other eluting slightly earlier (FIG. 2). Protein from the later peak migrated on SDS-PAGE mainly as a 60 kDa species and protein frown the earlier peak migrated as a single 25 kDa species (FIG. 1, lanes D and E respectively). Fragmentation of the human BPI holoprotein and isolation of the 25 kDa fragment could be repeated with the recovered human holoprotein upon repetition of this procedure, confirming that the 25 kDa fragment was human BPI-derived.

In like manner, rabbit BPI holoprotein, purified as in Example 1 above (500 ng, FIG. 1, lane F, before incubation) was fragmented after incubation for 24 hours at 37° C. in 0.1M HEPES-NaOH (pH 7.0) into a 25 kDa species (FIG. 1, lane G, after incubation).

EXAMPLE 3

NH$_2$-TERMINAL AMINO ACID COMPOSITION AND SEQUENCE ANALYSIS OF BPI FRAGMENTS

The human 25 kDa BPI fragment of the present invention was subjected to amino acid analysis, and the results were compared with the amino acid analysis of purified 60 kDa human holoprotein. Amino acid compositions were determined using a Waters Pico-Tag amino acid analyzer (Waters Associates, Milford, Mass.) as described (Bidlingmyer, B. A., et al., *J. Chrom.*, 336:93–104, 1984). Samples were pretreated in vacuo for 24 hours at 110° C. with 5.7N HCl containing 0.05% phenol. The results are shown in Table 1.

TABLE 1

Amino Acid Composition of the 25 kDa Fragment and of the Human BPI Holoprotein -

|     | 25 kDa Fragment | Human BPI Holoprotein |
|-----|-----------------|-----------------------|
|     | (% of total)    |                       |
| Asx | 8.7             | 9.1                   |
| Glx | 8.8             | 8.9                   |
| Ser | 15.2            | 8.8                   |
| Gly | 7.1             | 6.4                   |
| His | 2.9             | 2.8                   |
| Arg | 3.6             | 3.7                   |
| Thr | 3.5             | 4.6                   |
| Ala | 4.1             | 6.0                   |
| Pro | 5.0             | 8.1                   |
| Tyr | 2.6             | 2.7                   |
| Val | 5.8             | 7.3                   |
| Met | 2.3             | 2.4                   |
| Ile | 7.3             | 5.0                   |
| Leu | 7.7             | 10.3                  |
| Phe | 4.2             | 6.1                   |
| Lys | 11.4            | 7.6                   |

The values shown above represent the mole fraction (%) of each amino acid and are the mean of three independent determinations. "Asx" stands for asparagine and/or aspartic acid and "Glx" stands for glutamine or glutamic acid.

Amino acid analysis showed that the human 25 kDa fragment was enriched in lysine and serine and contained less non-polar residues when compared with the holoprotein (Table 1).

NH$_2$-terminal sequence analysis of the human BPI fragment of the present invention and of the holoprotein were performed using the well-known sequential Edman degradation technique (Edman, P. *Eur. J. Biochem.*, 1:80–91, 1967) using an amino acid sequencer (Beckman, Model 890C, Beckman Instruments Inc., Fullerton, Calif.) for the holoprotein or a gas phase sequencer (Applied Biosystems, Model 470A, Applied Biosystems, Inc., Foster City, Calif.) for the fragment. Phenylthiohydantoin derivatives of amino acids released sequentially by the Edman degradation process were analyzed by reversed-phase HPLC using an 150 mm C-18 column for human BPI (IBM Instruments Inc., Wallingford, Conn.) or an ODS column for the fragment of the present invention (Du Pont Zorbax ODS column, E. I. Du Pont de Nemours, Wilmington, Del.). The results are shown in Table 2 below.

TABLE 2

Holoprotein V N P G V V V R I S Q K G L D Y A S Q Q
25 Kd Fragment V N P G V V V R I S Q K G L D Y A S Q Q
V = Val, N = Asn, P = Pro, G = Gly, R = Arg, I = Ile,
Q = Gln, K = Lys, L = Leu, A = Ala, S = Ser As can be seen from the data in Table 2, the NH$_2$-terminal amino acid sequence of the human 25 kDa fragment of the present invention and the holoprotein derived from human PMN were identical in the first 20 amino acid residues (SEQ. ID NO. 5), indicating that the fragment was the NH$_2$-terminal portion of the human holoprotein.

EXAMPLE 4

BIOLOGICAL PROPERTIES OF THE BPI FRAGMENT OF THE PRESENT INVENTION

The antibacterial effects of the 25 kDa human BPI fragment of the present invention were compared with the known activities of the holoprotein. *E. coli* J5 (obtained from Dr. L. Leive, NIH Bethesda, Md. but any other *E. coli* strain could have been used) which produces short-chain lipopolysaccharides (LPS) in galactose-free culture medium, were grown overnight and then subcultured at 37° C. in triethanolamine-buffered media as described in Simon, E. G. et al., *Proc. Nat'l. Acad. Sci. (USA)*, 51:877, 1964). $5 \times 10^6$ *E. coli* J5 were incubated in a volume of 250 microliters with increasing amounts of either the human holoprotein or the human 25 kDa fragment of the present invention. The effects on bacterial viability were determined either by (1) diluting an aliquot ($5 \times 10^5$ bacteria) of the incubation mixture into 2 ml of nutrient broth (Difco Laboratories, Detroit, Mich.) and measuring bacterial growth (absorbance at 550 nM using a standard spectrophotometer after approximately 4 hours at 37° C.); or (2) plating diluted samples on nutrient agar and counting bacterial colonies after overnight incubation at 37° C. The results are presented in FIG. 3. In FIG. 3, open circles represent BPI holoprotein-treated bacteria and closed circles represent bacteria treated with the human 25 kDa fragment of the present invention.

Figure 3A:
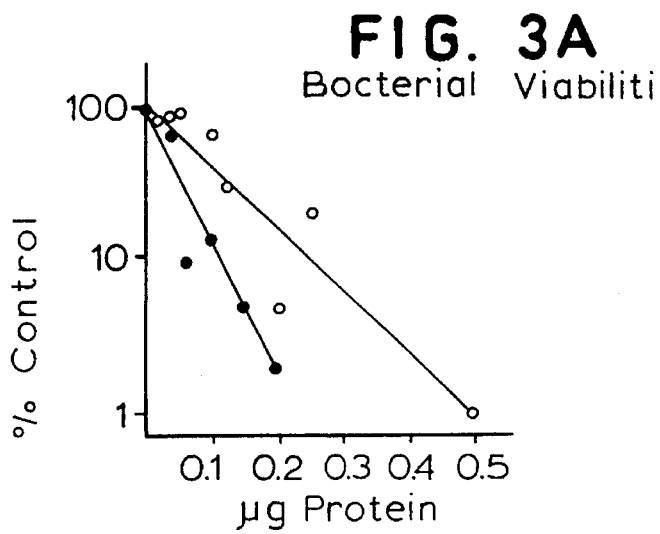
FIGS. 3a, 3b, 3c, and 3d are a series of graphs comparing the biological activities of the 25 kDa human BPI fragment of the present invention and the holoprotein toward *E. coli* J5. (3a) bactericidal activity (3b) effect on bacterial protein synthesis; (3c) permeability increasing activity; and (3d) phospholipase activation.

FIG. 3A shows that the isolated 25 kDa fragment of the present invention killed *E. coli* J5, a strain of bacteria highly sensitive to the holoprotein, in a dose-dependent manner. A linear regression analysis of the data presented in FIG. 3A further showed that the fragment was about twice as potent as the holoprotein on a mass basis, meaning that it is about equally potent on a molar basis because the fragment is about half the size of the holoprotein (FIG. 3A).

Figure 3B:
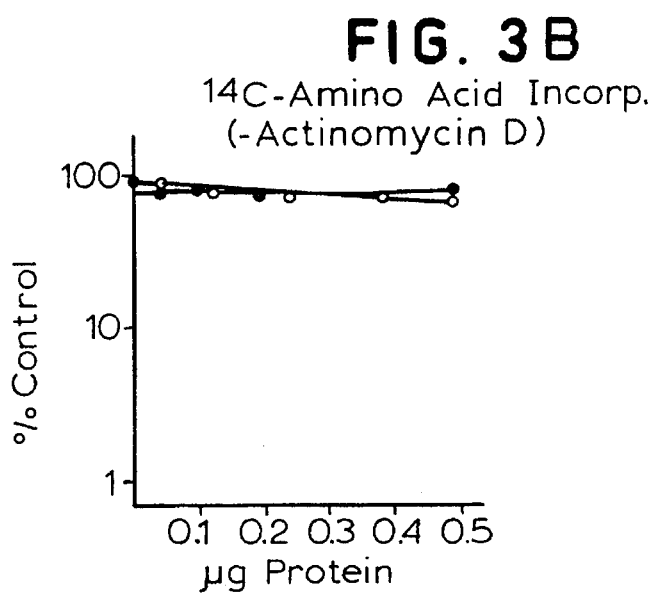

Killing of *E. coli* by mammalian BPI is initially accompanied by discrete alterations of the outer envelope without causing any apparent damage to the bacterial biosynthetic machinery. FIG. 3B shows that even at almost fully lethal doses, both the human holoprotein and the human 25 kDa fragment of the present invention caused little inhibition of bacterial protein synthesis. In contrast, both the fragment and the holoprotein caused nearly a complete inhibition of *E. coli* J5 protein synthesis when administered in the presence of 50 micrograms/ml of the antibiotic actinomycin D (Merck, Sharp and Dohme, St. Louis, Mo., FIG. 3C). This effect of actinomycin D reflects increased permeability of the outer membrane of the bacteria permitting the entry of the normally impermeant actinomycin D into the cell where it inhibited RNA and, consequently, protein synthesis. The dose-dependence of the permeability-increasing effect of the fragment of the present invention and the holoprotein was the same as that shown for the bactericidal activity above, and demonstrated that in this respect also the fragment was twice as active as the holoprotein, on a mass basis.

In order to compare the effects of the fragment of the present invention with the holoprotein on bacterial phospholipids, bacteria were prelabeled during growth with $(1-^{14}C)$-oleic acid (New England Nuclear, Boston, Mass.) as described in Elsbach, P. et al., *J. Biol Chem.*, 254:11000–11009, 1979. Incubation mixtures were supplemented with 0.4% bovine serum albumin (W/V) to capture phospholipid breakdown products ($^{14}$C-free fatty acids and $^{14}$C-lysocompounds) permitting their separation from unhydrolyzed bacterial $^{14}$C-phospholipids by filtration through a membrane filter (Millipore HAWP, Millipore Corp. Bedford, Mass.) to measure phospholipid degradation. The results are shown in FIG. 3D.

Figure 3D:
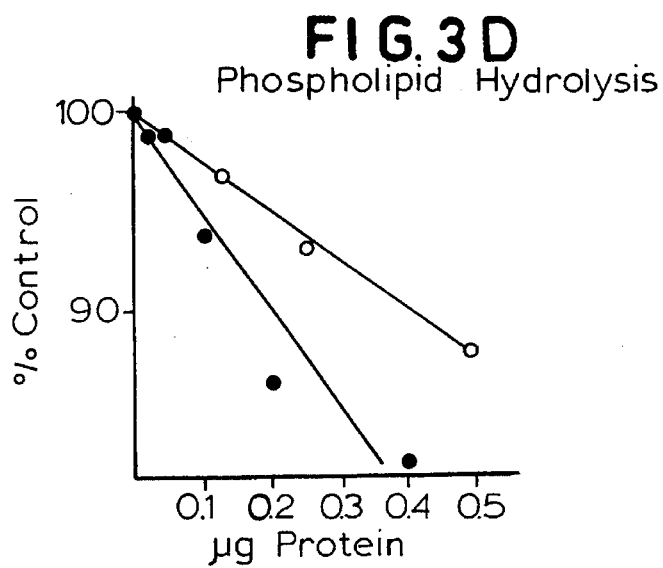
Figure 3C:
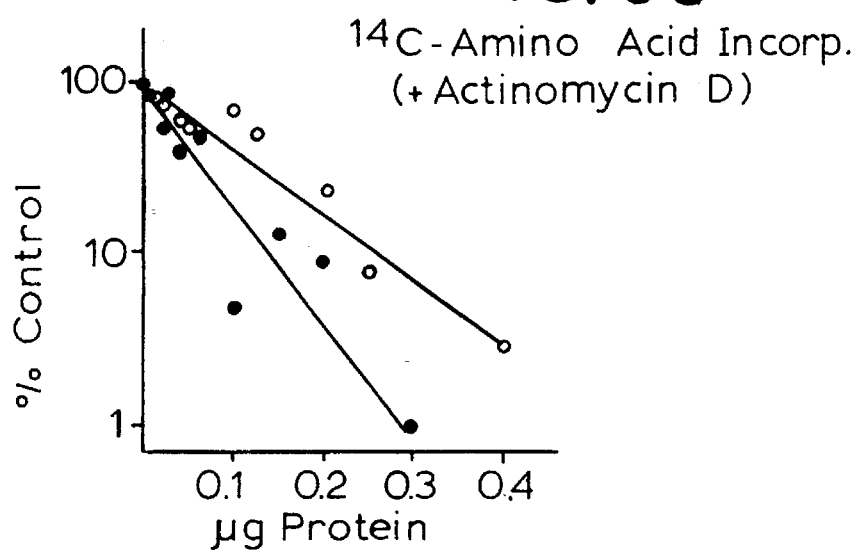

As shown in FIG. 3D, the dose-dependent activation of bacterial phospholipid degrading enzymes by the holoprotein was also produced by the 25 kDa fragment of the present invention, again requiring only half the mass of protein for a comparable effect.

The action of the BPI holoprotein on *E. coli* is hindered by the presence in the bacterial outer membrane of lipopolysaccharides with long polysaccharide chains ("smooth strains"). The effectiveness of the 25 kDa fragment of the present invention towards a smooth *E. coli* strain (0111:B4) was compared with that of the holoprotein. *E. coli* 0111:B4 is a smooth strain bearing longer polysaccharide chains than *E. coli* J5. Bacteria ($1 \times 10^6$) were incubated in 125 microliter mixtures with increasing amounts of the BPI holoprotein or the 25 kDa fragment of the present invention. Bacterial viability was measured as above and is expressed as percent of viability of bacteria incubated alone (without any additions). The results are shown in FIG. 4.

Figure 4:
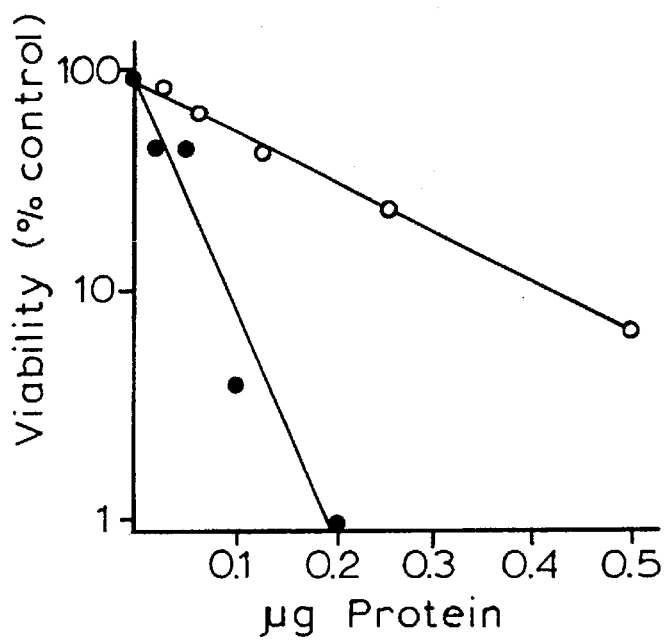
FIG. 4 is a graph comparing the bactericidal effect of the 25 kDa human BPI fragment of the present invention and the holoprotein on *E. coli* 0111:B4.

As can be seen in FIG. 4, the 25 kDa fragment of the present invention (closed circles) was about five times more potent than the holoprotein (open circles) towards *E. coli* 0111:B4. The five fold enhancement in activity of the 25 kDa fragment of the present invention with respect to the holoprotein, suggests that the smaller size of the fragment of the present invention is a factor in facilitating access of the fragment to binding sites at the base of the LPS polysaccharide chain.

In order to determine if the human 25 kDa fragment of the present invention retained the same cytotoxic specificity towards gram negative bacteria as the holoprotein, the activities of the 25 kDa fragment and the holoprotein toward a gram-positive bacterium, *Micrococcus lysodeikticus* (obtained from Dr. M. Salton, New York University, New York, N.Y.) were compared. The bacteria were grown in brain heart infusion broth (Difco Laboratories, Detroit, Mich.) at 37° C. Bacterial viability was measured as above for *E. coli*.

Neither the human 25 kDa fragment (5–10 micrograms) of the present invention nor the holoprotein (10–20 micrograms) produced any effect on the viability of *Micrococcus lysodeikticus*, even at doses twenty times greater than those that are fully lethal towards gram negative *E. coli* J5.

The data presented above demonstrate that the spectrum and potency of the antibacterial activities of the human 25 kDa BPI fragment of the present invention are at least equal to and sometimes substantially greater than those of the holoprotein. The data indicate that all of the molecular determinants required for BPI cytotoxicity reside within the portion of the BPI molecule included in the fragment of the present invention.

EXAMPLE 5

CLONING OF THE cDNA OF HUMAN BPI AND IDENTIFICATION OF THE AMINO ACID SEQUENCE

Two synthetic oligonucleotides (SEQ. ID NOS: 6 and 7) were designed to encode the 33 amino terminal residues of human BPI. The probes BPI-1 (GTCAATCCTGGTGT-TGTGGTCAGGATCTCTCAGAAGGGCCTGGATTA TGCCTCCCA) and BPI-2 (GCAAGGCACAGCTGCCCT-GCAGAAGGAGCT GAAGAGGATCAAGATTCCTGAC-TAT) were each designed to encode half of the known human BPI sequence as previously disclosed in Ooi, C. E. et al., (*J. Biol. Chem.*, 262:14891–14894, 1987). The probes were kinase labeled with $^{32}$P using standard techniques well-known in the art and used to independently screen a human genomic liver library as disclosed in Lawn. R. M. et al. (*Cell*, 15:1157–1174, 1978). Six clones were identified among 500,000 plaques which hybridized independently with each probe. The hybridizing region of one of these clones was sequenced and clearly encoded the amino terminal end of human BPI. This sequence was interrupted by an intron or intervening sequence but nevertheless predicted an additional 22 amino acid residues which preceded the next intron or intervening sequence.

Based on the gene sequence, a new DNA probe was then synthesized which corresponded exactly to the encoded 55 amino terminal residues. This probe was used to screen a small cDNA library prepared from human HL-60 cells (available as ATCC CCL 240, American Type Culture Collection, Rockville, Md.) induced with dimethylsulfoxide, DMSO. In the library of the 300,000 plaques, 4 clones were isolated which hybridized with the exact probe. DNA from the clones was isolated and the hybridizing regions were sequenced by the dideoxy chain terination technique of Smith. A. J. H. (*Meth. Enzym.*, 65:560–580, 1980). The sequence of the longest clone is presented in FIG. 5.

As shown in FIG. 5, the sequence predicts a 31 amino acid signal peptide, followed by a 456 residue mature protein (the amino acids and encoding DNA of which are respectively set out in SEQ. ID NOS: 2 and 1). The amino terminal sequence determined by protein sequencing of human BPI matches the encoded cDNA exactly. Furthermore, the deduced amino acid composition of the encoded protein corresponds closely to the amino acid composition determined for purified human BPI as disclosed in Ooi. C. E. et al., 1987, supra. The encoded sequence predicts a protein of 50.6 kD; the estimated molecular size of purified human BPI is approximately 58 kD. This difference in the apparent size may reflect the presence of two potential N-linked glycosylation sites at positions 122 and 349 of the protein (indicated by overlines in FIG. 5).

To further demonstrate that this cDNA encoded human BPI, its expression was engineered in mammalian cells. The entire cDNA was subcloned in a mammalian cell expression vector (Wood. W. I. et al., *Nature*, 312:330–337, 1984), and then transfected into a human kidney cell line. Small amounts of recombinant BPI were transiently produced and characterized by Western Blotting techniques, showing an immunoreactive band with a mobility identical to that of native human BPI (results not shown).

The natural expression of BPI in various human tissues was then analyzed by Northern Blot hybridization. RNA was prepared from various tissues (Chirgwin. J. M. et al., Biochem., 24:5294–5299, 1979), passed over oligo-dT-cellulose and electrophoresed through a formaldehyde agarose gel (Dobner. P. R. et al., *Proc. Nat. Acad. Sci. (USA)*, 78:2230–2234, 1981). The gel was transferred to nitrocellulose as described (Thomas, P. S., *Proc. Nat. Acad. Sci. USA*, 77:5201-52-5, 1980) and hybridized under stringent conditions with BPI cDNA.

Figure 6A:
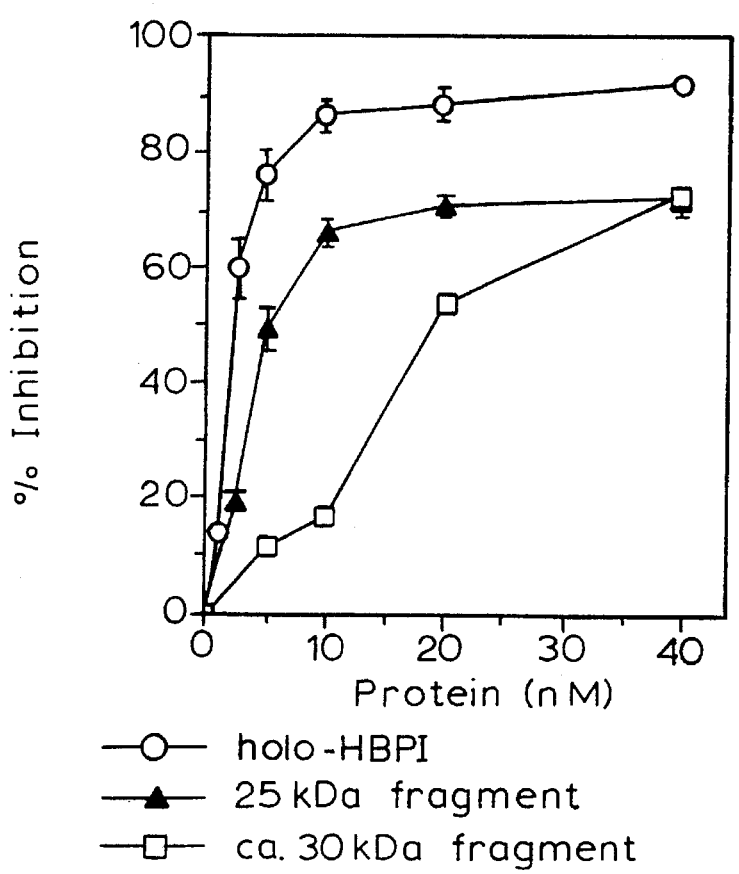
FIGS. 6A and 6B are plots of the inhibition of LPS-mediated activation against concentration of BPI (or BPI fragment).
Figure 6B:
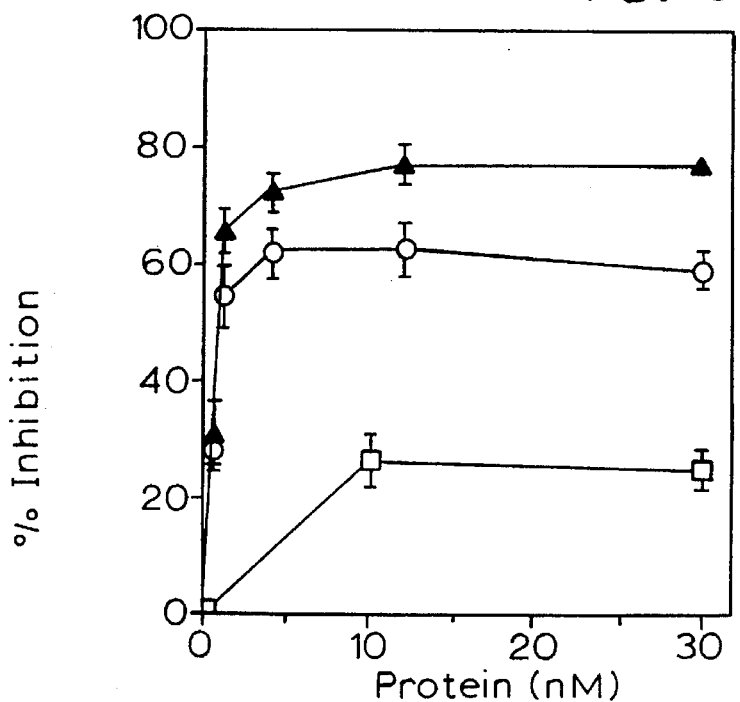

As shown in FIGS. 6A and 6B, the BPI cDNA probe hybridized well with mRNA ;prepared from the spleen of a patient with chronic myelocytic leukemia. The spleen was heavily infiltrated with immature myeloid cells. The size of the hybridizing signal was approximately 2,000 bases in length, suggesting that the cDNA sequence presented in FIG. 5 was full length. The BPI probe did not hybridize with mRNA from normal spleen, mature peripheral blood leukocytes, liver, kidney, or brain. This result is in agreement with previous observations on the location of BPI in various cell types and tissues; the presence of BPI has been previously shown to be restricted to cells of the myeloid series. The BPI cDNA was also used as a probe in Southern hybridizations of human genomic DNA. DNA was isolated from human peripheral blood leukocytes, as described in Blin. N. et al., *Nuc. Acids Res.*, 3:2303–2308, 1976), digested with restriction endonucleases Eco RI, BamHI and HindIII, and fractionated on a 1% agarose gel. The DNA was transferred to nitrocellulose (as described in Southern, E. M., *J. Molec. Biol.*, 98:503–517, 1975) and hybridized with a 5' end fragment of the BPI cDNA probe under stringent conditions (as described in Maniatis et al, Molecular Cloning, a laboratory Manual, pp. 387–389, Cold Spring Harbor Laboratories, New York, 1982).

A single hybridizing band was observed in restriction digests using Eco RI and BamHI when the 5' end of the BPI cDNA was utilized as a probe. This suggested that BPI was encoded by a single gene.

The primary structure of the human BPI protein sequence reveals several features which may be critical for its function. As mentioned above, an amino terminal 25 kD fragment contains all of the anti-bacterial activity of the holoprotein. A clear charge asymmetry can be observed when the amino terminal 25 kD fragment is compared with the holoprotein. The amino terminal end contains 17 more basic than acidic residues (28 lysine/arginine vs. 11 aspartate/ glutamate), while the carboxy terminal end is slightly acidic (20 basic vs. 23 acidic residues). The very basic nature of the amino terminal domain may promote an electrostatic interaction of BPI with the negatively charged LPS in the bacterial envelope.

Paper Example I

CO-TREATMENT OF GRAM NEGATIVE BACTERIA WITH THE HUMAN BPI FRAGMENT AND PENICILLINS

The human BPI fragment of the present invention will be used to test the effectiveness of compositions containing the fragments and Penicillin-G or a hydrophobic derivative, Penicillin-V. Both smooth (*E. coli* 0111:B4) and rough (*E. coli* J5) gram negative bacteria will be seeded and incubated as in Example 3 above with serial two-fold dilutions containing: the human 25 kDa BPI fragment of the present invention (1 microgram–1000 micrograms) alone, Penicillin-G (3,000–300,000 units) alone, Penicillin-V Benzathine (300,000 units) alone and compositions containing the same concentrations of the above as mixtures, e.g., the BPI fragment plus Penicillin-G and the BPI fragment plus Penicillin-V. Bacterial viability will be monitored as above in Example 3.

It is expected that lower amounts of both of the penicillins will be effective in killing both smooth and rough *E. coli* strains in the presence of the human 25 kDa BPI fragments showing the efficacy of this embodiment of the present invention.

EXAMPLE 6

PREPARATION OF LPS AND OTHER MATERIALS USED IN EXPERIMENTS DESCRIBED BELOW

Purified LPS from *E. coli* 055:B5 (S chemotype) was commercially obtained from Calbiochem. Corp. (La Jolla, Calif.) and resuspended in pyrogen-free water with vigorous vortexing according to the instructions of Whittaker Bioproducts, Inc. (Walkersville, Md.) as provided in the manufacturers pamphlet. Serial dilutions of LPS were prepared in the same way and stock solutions of LPS (10 ng/ml) were stored at 4° C.

LPS from *Salmonella minnesota* mutant $R_e595$ ($R_e595$ chemotype) was commercially obtained frown List Biologicals (Campbell, Calif.). Solutions of this LPS were prepared by sonication as previously described (Doerfler, M. E., Danner, R. L., Shelhamer, J. H., and Parrillo J. E., *J. Clin. Invest.*, 83:970–977, 1989).

The chromogenic Limulus amebocyte lysate ("LAL") assay kit was from Whittaker Bioproducts, Inc.

Zymosan was from Sigma Chem. Co. (St. Louis, Mo.), and opsonization was carried out as previously described (Marom, Z., Shelhamer, J. H., and Kaliner, M., *J. Exp. Med.*, 159:844–860, 1984) and in accordance with the manufacturer's instructions.

$LTB_4$ (LEUCOTRIENE $B_4$) standards including $LTB_4$ derivatives were from Calbiochem. Corp. Tumor necrosis factor (to about $4 \times 10^7$ U/mg) was obtained from J. Vilcek, Department of Microbiology, NYU Medical Center (obtained as described in Alerka, D., Le, J. and Vilcek, J., *J. Immunol.*, 143:3517–3523, 1989). Hanks' balanced salts solution (minus $Ca^{2+}$ and $Mg^{2+}$) (HBSS-) was from Gibco (Grand Island, N.Y.). Acetonitrile was from J. T. Baker, Inc. (Philipsburg, N.J.), trifluoroacetic acid from Pierce (Rockford, Ill.), and bovine serum albumin from United States Biochemical Corp. (Cleveland, Ohio).

The Bio-Rad protein assay kit used in the Examples below was from Bio-Rad Laboratories (Richmond, Calif.), protein (molecular weight) standards were from Diversified Biotech Inc. (Newton Center, Mass.), and nitrocellulose was from Schleicher & Schuell (Keene, N.H.). Nutrient broth and BiTek agar were from DIFCO (Detroit, Mich.).

The reversed-phase Vydac C4 column was from The Separations Group, Hesperia, Calif.

Polymorphonuclear leukocytes were isolated from the venous blood of normal volunteers using standard procedures of dextran sedimentation and centrifugation on Ficoll-Hypaque as previously described (Doerfler, M. E., Danner, R. L., Shelhamer, J. H., and Parrillo J. E., *J. Clin. Invest.*, 83:970–977, 1989).

Human BPI was purified from crude extracts of PMN-rich human leukocyte populations using *E. coli* as an affinity matrix, as described in Example 1 or as previously described (Mannion, B. A., Kalatzis, E. S., Weiss, J. and Elsbach, P., *J. Immunol.*, 142:2807–2812). The 25-kDa $NH_2$-terminal fragment of human BPI was isolated after limited proteolysis of purified human BPI as described in Example 2 above and in Ooi, C. E., Weiss, J., Elsbach, P., Frangione, B. and Mannion, B., *J. Biol. Chem.*, 262:14891–14894, 1987.

Eluted BPI was immediately dialyzed against 50 volumes of 10–50 mM sodium acetate, pH 4.0. The 25-kDa N-terminal fragment of human BPI was immediately dried in a Speed Vac evaporator/concentrator (Savant Instruments, Inc., Farmingdale, N.Y.). The dried protein was resuspended in 10 mM sodium acetate, pH 4.0 with no apparent loss of biological activities.

All protein samples were stored at 4° C.
Bacterial Cultures:
*E. coli* J5, a "rough" (short-chain LPS) UDP-4-galactose-epimeraseless mutant of the "smooth" (longchain LPS) parent *E. coli* 0111:B4, was grown overnight, and then in subculture at 37° C. in triethanolamine-buffered medium as described in Weiss, J. Beckerdite-Quagliata, S. and Elsbach, P., *J. Clin. Invest.*, 65:619–628, 1980. Bacterial subcultures were harvested at mid-logarithmic phase and resuspended to the desired concentration in sterile physiological saline.

Bioassays:

(a) Bacterial growth inhibition:

Bacteria were incubated with the protein to be tested in each case for 15 minutes at 37° C. in the standard incubation mixture containing 0.8% (w/v) nutrient broth in saline buffered with 20 mM sodium phosphate, pH 6.0. After the incubation, bacteria were serially diluted with sterile physiological saline to $4 \times 10^3$ organisms/ml, then plated on nutrient agar (0.8% (w/v) nutrient broth, 0.5% (w/v) NaCl, 1.5% (w/v)/BiTek agar) by pouring 5 ml molten nutrient agar (48° C.) into a sterile petri dish containing 30 microliters of the diluted bacteria. Bacterial growth was measured as the number of colony forming units enumerated after overnight incubation at 37° C.

(b) Bacterial Outer-Membrane Permeability-Increasing Activity:

Permeability of the *E. coli* outer membrane to the normally impermeant antinomycin D was assessed by measuring sensitivity of these bacteria to actinomycin D. Bacterial growth was measured as described above, with 50 micrograms/ml actinomycin D and 500 micrograms per ml serum albumin present in the standard incubation mixture as described in Mannion, B. A., Weiss, J. and Elsbach, P., *J. Clin. Invest.*, 85:853–860, 1900.

(c) LPS-neutralization by BPI:

Incubation of LPS with BPI was carried out in polypropylene tubes at the desired BPI and LPS concentrations, in 10 mM sodium phosphate, pH 7.0 (*E. coli* LPS) or in HBSS⁻ (minus $Ca^{2+}$ and $Mg^{2+}$) (Salmonella LPS), for 15 minutes at 37° C.

(c') LPS-induced release of tumor necrosis factor (TNF) in whole blood. LPS-triggered release of TNF in whole blood ex vivo was carried out as described by Desch et al. (*Lymphokine Res.*, 8:141, 1989) except that blood was collected into tubes containing citrate as an anti-coagulant (Becton-Dickinson, Lincoln Park, N.J.). Detection of TNF by ELISA was carried out using a commercially available test kit (Biokine TNF Test Kit, T Cell Sciences, Cambridge, Mass.).

EXAMPLE 7

ENDOTOXIN-NEUTRALIZING ACTIVITY OF THE 25-kDa N-TERMINAL FRAGMENT OF HUMAN BPI (d) Protease Activation in a Limulus Amebocyte Lysate:

To determine whether the antibacterial 25-kDa N-terminal fragment of human BPI also possessed the potent endotoxin neutralizing activity of the holoprotein, the effects of these two protein species were initially compared on LPS-mediated activation of protease(s) in Limulus amebocyte lysates. (See Example 6 for details). The recent observations of Marra et al. (Marra, M. N., Wilde, C. G., Griffith, J. E., Snable, J. L., and Scott, R. W., *J. Immunol.*, 144:662–666, 1990) were reproduced showing that 10 nM holo-BPI produced nearly complete inhibition of the activity of LPS from *E. coli* 0111:B4 (S chemotype) in this assay (data not shown). Brief preincubation of varying amounts of BPI with LPS from *E. coli* 055:B5 (S chemotype) and from *S. minnesota* $R_e$ 595 ($R_e$ chemotype) produced dose-dependent inhibition of the activity of these LPS species as well.

The results are shown in FIG. 6A (*E. coli* LPS) and FIG. 6B (*S. minnesota* LPS). Half-maximal inhibition of both LPS species was produced by 1–2 nM BPI but, at maximum (5–10 nM BPI), inhibition of the LPS from smooth *E. coli* was more complete. The 25-kDa N-terminal fragment also displayed potent endotoxin-neutralizing activity in this assay. The fragment was nearly as active as the holoprotein against the LPS from *E. coli* 055:B5 and even slightly more active than holo-BPI toward the LPS from *S. minnesota* $R_e$ 595.

LPS from *E. coli* 055:B5 (1 ng/ml) (FIG. 6A), or *S. minnesota* mutant $R_e$ 595 (0.6 or 2 ng/ml) (FIG. 6B), were pre-incubated with increasing amounts of human BPI (open circles), 25-kDa N-terminal fragment (closed triangles), or approximately 30-kDa C-terminal fragment(s) (open squares). Preincubations were in 10 mM sodium phosphate buffer, pH 7.0 (FIG. 6A) or Hanks' balanced salt solution (minus $Ca^{2+}$ and $Mg^{2+}$) (FIG. 6B) at 37° C. for 15 minutes. The LPS-protein incubation mixtures were then diluted to give LPS concentrations of 0.1 ng/ml (FIG. 6A), or 0.03 ng/ml (FIG. 6B) for measurement of LPS activity in the Limulus assay described in Example 6 conducted in accordance with the manufacturer's instructions.

(e) Priming of Polymorphonuclear Leukocytes

Figure 7A:
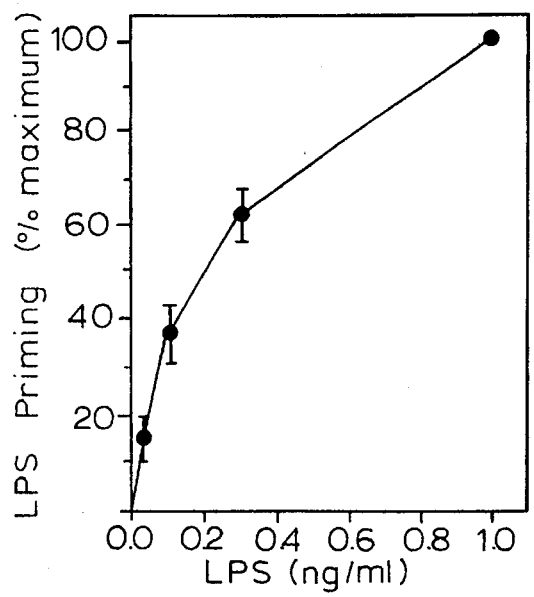
FIGS. 7A and 7B are plots of the ability of PMN to be primed as a function of the LPS concentration (7A) or as a function of BPI or BPI fragment (7B) in the PMN-containing medium.

To further substantiate the endotoxin-neutralizing properties of BPI and its fragments, the ability of these protein species to inhibit the priming of PMN by LPS was also tested. Priming refers to the ability of low doses of LPS to increase the responsiveness of the target cell (e.g., PMN) to a subsequently added second stimulus as described in Guthrie, L. A., McPhail, L. C., Henson, P. M., and Johnston, J. R., *J. Exp. Med.*, 160:1656–1671, 1984. For example, the release of $LTB_4$ and its metabolites by human PMN during incubation with opsonized zymosan is significantly increased by pretreating the PMN with LPS (Doerfler, M. E., Danner, R. L., Shelhamer, J. H., and Parrillo J. E., *J. Clin. Invest.*, 83:970–977, 1989; FIG. 7A). This effect of LPS is dose-dependent (FIG. 7A) thus providing a quantitative assay of endotoxin activity in which the amount of $LTB_4$ (and metabolites) released by unprimed cells (i.e., preincubation with buffer alone) is subtracted from the actual amount of $LTB_4$ (and metabolites) released, to yield the amount of $LTB_4$ (and metabolites) released as a result of LPS priming.

The release of leukotriene B4 ($LTB_4$) (and its metabolites) by PMM in response to opsonized zymosan after LPS priming was measured as previously described in Doerfler, M. E., Danner, R. L., Shelhamer, J. H., and Parrillo J. E., *J. Clin. Invest.*, 83:970–977, 1989. Briefly, LPS from *S. minnesota* mutant $R_e$595 in 0.5 ml was added to an equal volume of PMN suspension in HBSS-($5 \times 10^6$ PMN) and incubated for 45 minutes at 37° C. in a shaking water bath. Following incubation, $Ca^{2+}$ and $Mg^{2+}$ salts were added to a final concentration of 1.25 and 0.4 mM, respectively (representing amounts present in HBSS+). Opsonized zymosan was added (5 mg/ml) and the mixture was incubated for an additional 45 minutes at 37° C. in a dry bath. Incubations were terminated by addition of 1.5 volumes of iced ethanol (with 200 ng prostaglandin B2/sample, obtained from Calbiochem, as an internal standard) and extracts were prepared as described in Doerfler, supra. $LTB_4$ and metabolites were separated using a Waters HPLC system (Waters/Millipore, Morristown, N.J.), and identified and quantitated by comparison to appropriate standards (Shak. S., *Methods Enzymol.*, 141:355–371, 1987).

Figure 7B:
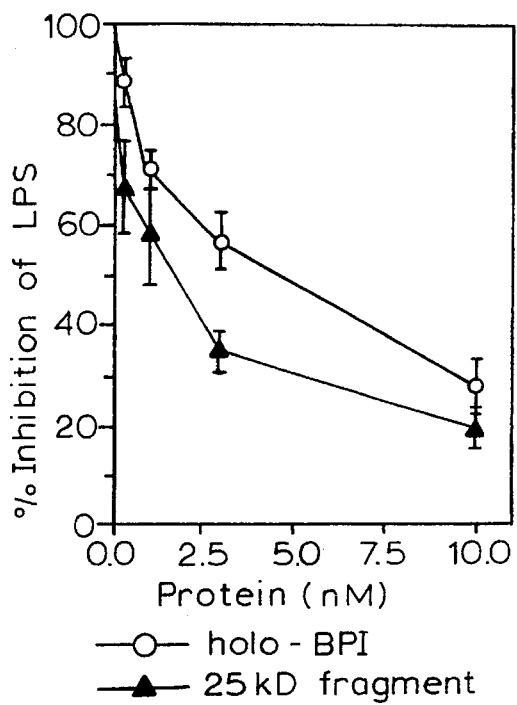
Figure 7C:
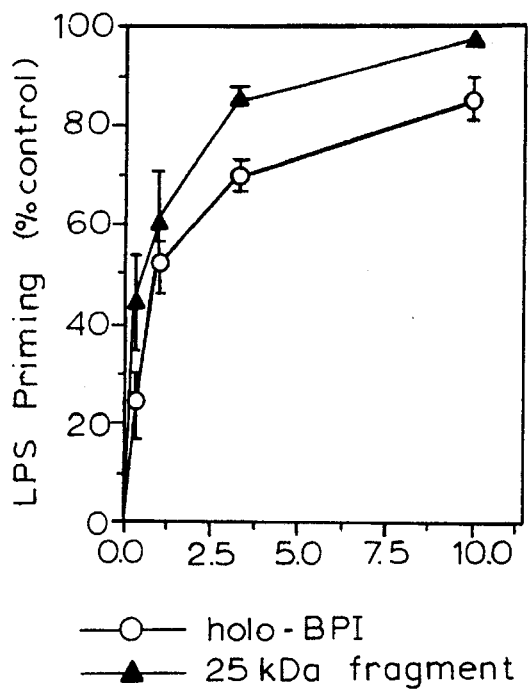
FIG. 7C is a plot of the inhibition of LPS priming activity as a function of the BPI or BPI-fragment concentration.

Pretreatment of PHN with either holo-BPI or the 25-kDa fragment did not affect the basal response of PMN to opsonized zymosan (data not shown) but brief pretreatment of $R_e595$ LPS with either protein produced a dose-dependent suppression of the primed response of PMN to opsonized zymosan (FIG. 7B). Priming of PMN by tumor necrosis factor (1 ng/ml) was unaffected by BPI (data not shown; Marra, M. N., Wilde, C. G., Griffith, J. E., Snable, J. L., and Scott, R. W., *J. Immunol.*, 144:662–666, 1990) indicating that the suppression of LPS priming by BPI and its N-terminal fragment was due to a direct effect on endotoxin. Fifty % inhibition of endotoxin activity was produced by approximately 1.0 and 0.3 nM holo-BPI and 25-kDa N-terminal fragment, respectively, and nearly complete inhibition was produced by 10 nM doses of each protein species (FIG. 7C). Comparison of the protein dose curves shows that in this assay the fragment is about 2 to 3 times more active, on a molar basis, than holo-BPI (FIGS. 7B and 7C).

More specifically, the data depicted in FIG. 7A–C were generated as follows:

For FIG. 7A: Release of $LTB_4$ (and metabolites) was measured after pre-incubation of PMN with varying amounts of $R_e595$ LPS. Priming of $5\times10^6$ PMN by 1.0 ng/ml LPS resulted in release of 31.0±4.5 ng $LTB_4$ and metabolites (n=4), representing an enhancement of 5–10 fold over unprimed cells. Values in FIG. 7A are expressed as % of maximum release, i.e., amount of $LTB_4$ released in response to 1 ng/ml LPS.

For FIG. 7B: LPS (0.6 or 2 ng/ml) was pre-incubated alone or with the indicated concentrations of holo-BPI and the 25-kDa fragment, at 37° C. for 15 minutes before adding LPS to the PMN suspension (final LPS concentration 0.3 or 1.0 ng/ml). The effect of added protein was the same at both LPS doses, and therefore these data were pooled. LPS priming in FIG. 7B is expressed as % of control, i.e., priming by LPS without preincubation with protein.

Figure 2A:
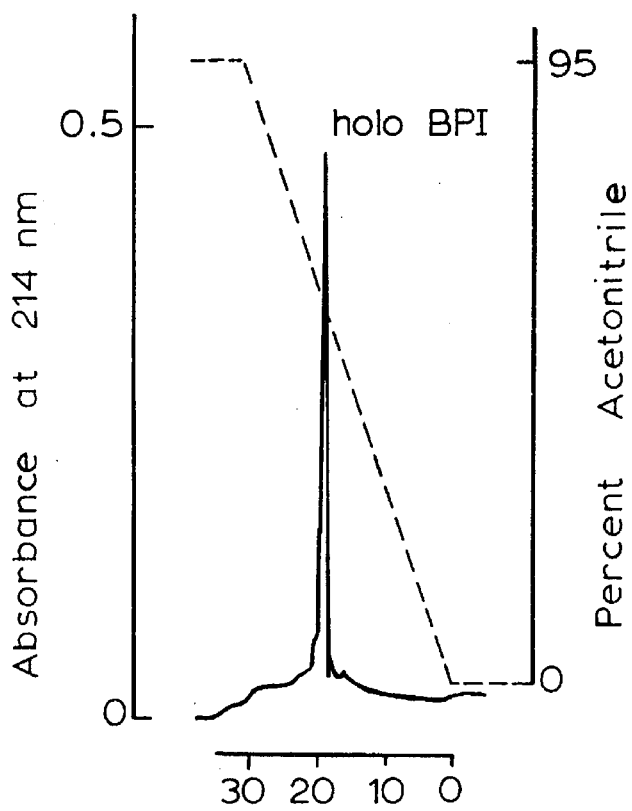
FIGS. 2A and 2B are graphs showing the chromatographic behavior of the human BPI holoprotein (2A) and human 25 kDa BPI fragment of the present invention (2B) on reversed phase HPLC.
Figure 2B:
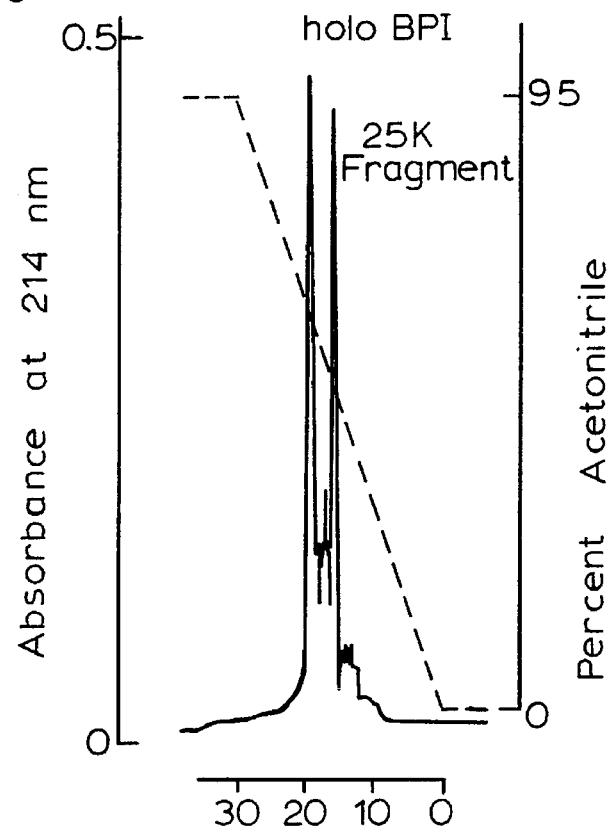

For FIG. 7C: Inhibition by BPI or its fragments of LPS priming was calculated by comparing the magnitude of LPS printing in the presence of added protein (FIG. 2B) to the LPS standard curve (FIG. 2A).

Each value shown in FIG. 7C represents the mean±SEM of six or more determinations.

EXAMPLE 8

PURIFICATION OF APPROXIMATELY 30-kDa C-TERMINAL FRAGMENT(S) OF HUMAN BPI

Figure 8A:
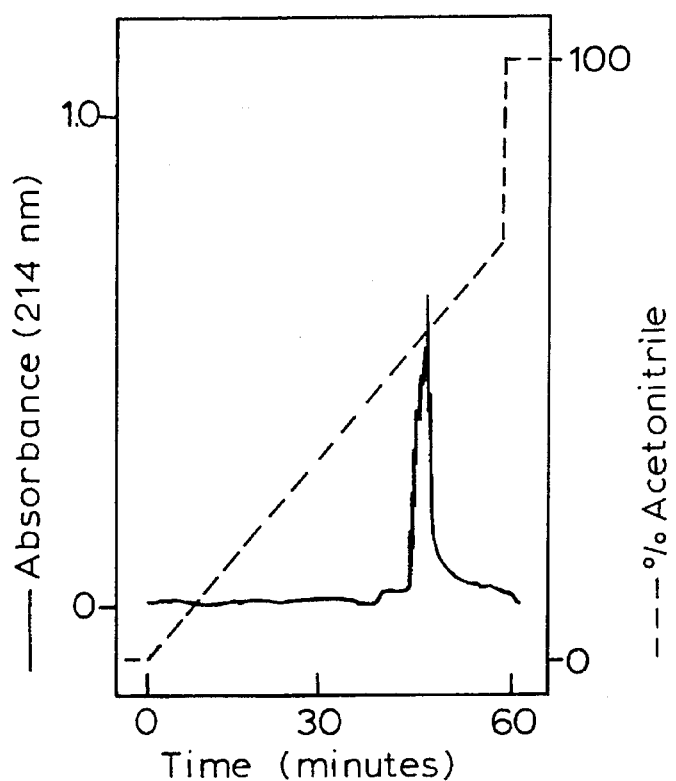
FIGS. 8A and 8B show two chromatographic elution profiles (protein elution monitored by absorbance at 214 nm showing the co-elution (FIG. 8A) and subsequent resolution (FIG. 8B) of the approx. 30 kD C-terminal moiety of BPI and of BPI itself.
Figure 8B:
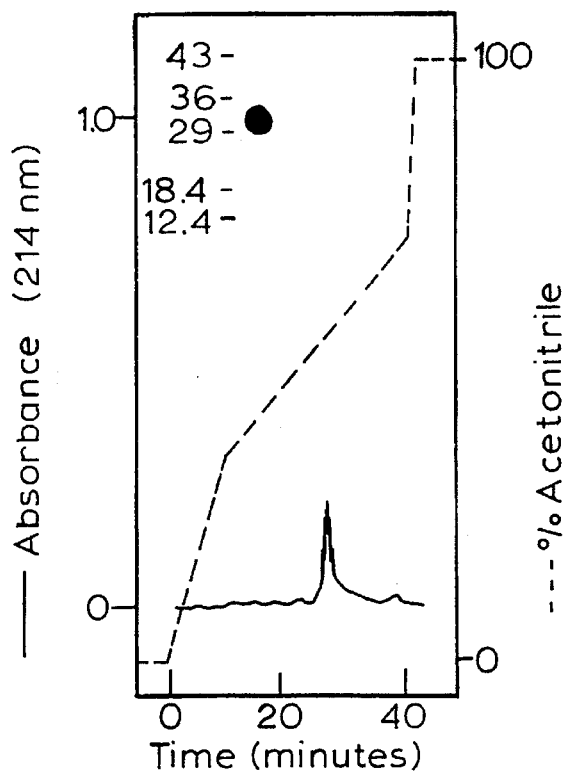

To permit a more complete assessment of the structural and functional properties of human BPI, the C-terminal portion of the protein was isolated and tested as provided in Examples 6 and 7. During the limited proteolysis that gives rise to the active 25-kDa N-terminal fragment, similar amounts of an approximately 30-kDa species also accumulate (Ooi, C. E., Weiss, J., Elsbach, P., Frangione, B. and Mannion, B., *J. Biol. Chem.*, 262:14891–14894, 1987). Whereas the 25-kDa fragment was readily isolated from the digest by reversed-phase HPLC, the approximately 30-kDa species co-eluted with the holo-protein (FIG. 8A representing chromatography of about 100 micrography of protein) Ooi, 1987, supra. Re-chromatography of the active fractions with a shallower (0–40 min) acetonitrile gradient was used to resolve the 60 kDa and approximately 30-kDa proteins (FIG. 8A, vs FIG. 8B broken line). The peak absorbing at 214 nm and eluting earlier migrated as a 60 kDa species upon SDS-PAGE and the latter peak migrated as a slightly heterogeneous approximately 30-kD species (FIG. 8B representing reversed phase HPLC of about 25 micrograms of protein).

The molecular weight of this protein fraction was determined by SDS-PAGE/Western blot (inset in FIG. 8B).

SDS-PAGE of proteins (12% polyacrylamide gel, system of Laemmli, Laemmli, U.K., *Nature*, 227:680–685, 1970, followed by transfer of proteins to nitrocellulose was carried out as previously described in Towbin, H., Staehelin, T., and Gordon J., *Proc. Nat'l. Acad. Sci.* (*USA*), 76:4350–4354, 1979.

Protein mass was estimated either by the Lowry method (Lowry, O. H., Rosebrough, N. J., Farr, A. L. and Randall, R. J., *J. Biol. Chem.*, 193:265–275, 1951) or the Bio-Rad protein assay kit (Example 6) with bovine serum albumin as the standard. Confirmation of estimates was obtained using Coomasie blue staining after SDS-PAGE, as well as absorbance at 214 nm.

Immunodetection of proteins with rabbit anti-BPI/[$^{125}$-I] -Protein G was carried out as previously described (Weiss, J. and Olsson, I., *Blood*, 69:652–659, 1987). The numbers indicate migration of protein standards monitored by Coomassie blue staining.

N-terminal amino acid sequencing of the latter protein fraction (performed by sequential Edman degradation on an Applied Biosystems Model 470A, Applied Biosystems, San Francisco, Calif.) revealed the presence of two overlapping species, one originating from residue 200 and the other from residue 204 of human BPI (Table 3, Gray, P. W., Flaggs, G., Leong, S. R., Gumina, R. J., Weiss, J., Ooi, C. E. and Elsbach, P., *J. Biol. Chem.*, 264:9505–9509, 1988). The size and location of the approximately 30-kDa fragment indicated therefore that it represents the C-terminal half of the BPI molecule. The later elution of the C-terminal moiety during reversed-phase HPLC is consistent with the greater hydrophobicity of this portion of holo-BPI, Ooi, (1987), supra; Gray, (1988), supra.

In Table 3, the sequence of residues 198–213 (see SEQ. ID NO:1) of human BPI shown was deduced from its cDNA sequence (Gray, P. W., Flaggs, G., Leong, S. R., Gumina, R. J., Weiss, J., Ooi, C. E. and Elsbach, P., *J. Biol. Chem.*, 264:9505–9509, 1988). The single letter designation for amino acids is used.

TABLE 3

| Human PBI | 200 | 210 |
|---|---|---|
| (residues 198–213) | K I D S V A G I N | Y G L V A P P |
| ca.30-kDa Fragment (1st) | D S V ( ) G I N | Y G L V |
| ca.30-kDa Fragment (2nd) | A G I ( ) | Y G L V A P (P) |

Antibacterial activities of the approximately 30 Kd fragments

*E. coli* J5 ($5\times10^6$) were incubated in the standard incubation mixture (see Example 6) (125 microliters) with increasing amounts of the 25-kDa fragment (closed circles) or the approximately 30-kDa fragment in the absence (closed triangles) or presence (open squares) of actinomycin D (50 micrograms/ml). Growth inhibitory effects (closed symbols) were measured by assessing colony formation on nutrient agar. Since the approximately 30-kDa fragment did not show any growth inhibitory effect, outer membrane permeability-increasing effects (open symbols) could be assessed by measuring bacterial viability in the presence of actinomycin D. The data are presented in FIG. 9 as percent of values obtained for bacteria incubated alone, and are the mean of two similar experiments.

Figure 9:
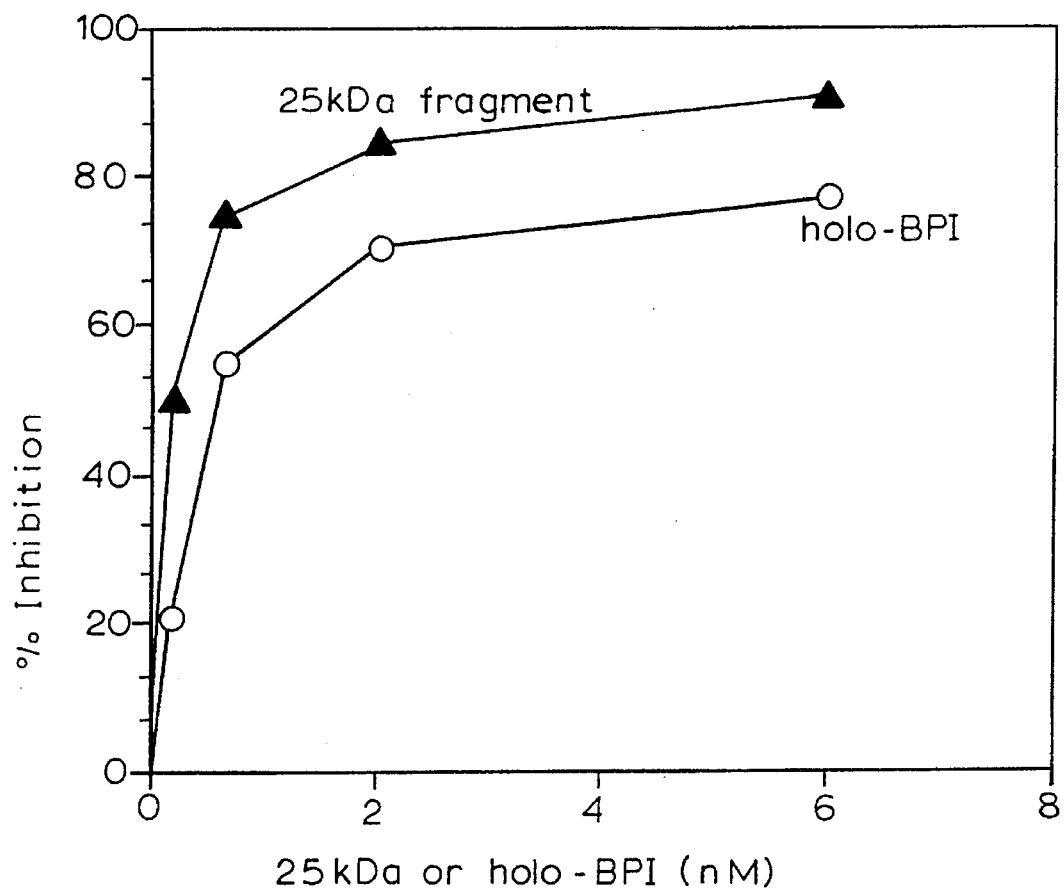
FIG. 9 is a plot comparing the antibacterial properties of the 25 kD N-terminal fragment of BPI and the approx. 30 kD C-terminal moiety as a function of concentration.

As shown in FIG. 9, in contrast to the 25-kDa N-terminal fragment, the purified C-terminal fragment(s) displayed no antibacterial activity toward BPI-sensitive *E. coli*. The C-terminal fragment(s) produced neither growth inhibitory nor outer membrane permeability-increasing effects on *E. coli* J5, even when tested at doses fifteen times higher than an effective dose of the 25-kDa fragment.

The isolated approximately 30-kDa C-terminal fragment(s) also displayed only limited endotoxin-neutralizing activity toward $R_e595$ LPS in the LAL assay (FIG. 1b) and no inhibitory effect toward this LPS in the PMN priming assay (data not shown). The C-terminal fragment(s) did produce, however, up to about 80% inhibition of the activity of *E. coli* 055:B5 LPS in the LAL assay, albeit at a 4–8 fold lower molar potency than the N-terminal fragment and holo-BPI, respectively (FIG. 6A).

Figure 10A:
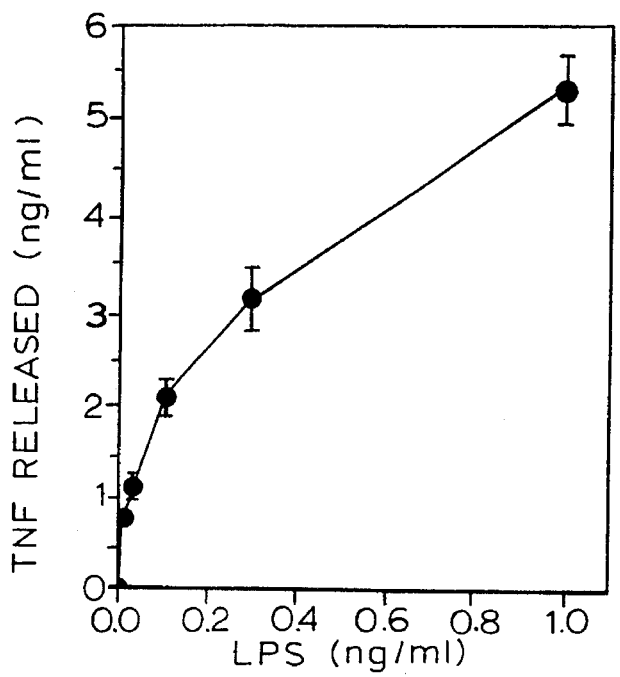
FIGS. 10A and 10B are graphs showing (10A) the dose-dependent synthesis and extracellular release of TNF triggered by LPS in whole blood and (10B) the dose dependence of Holo-BPI, the 25 kD N-terminal fragment and the 30 kD C-terminal fragment of human BPI on the release of TNF triggered by LPS in whole blood.
Figure 10B:
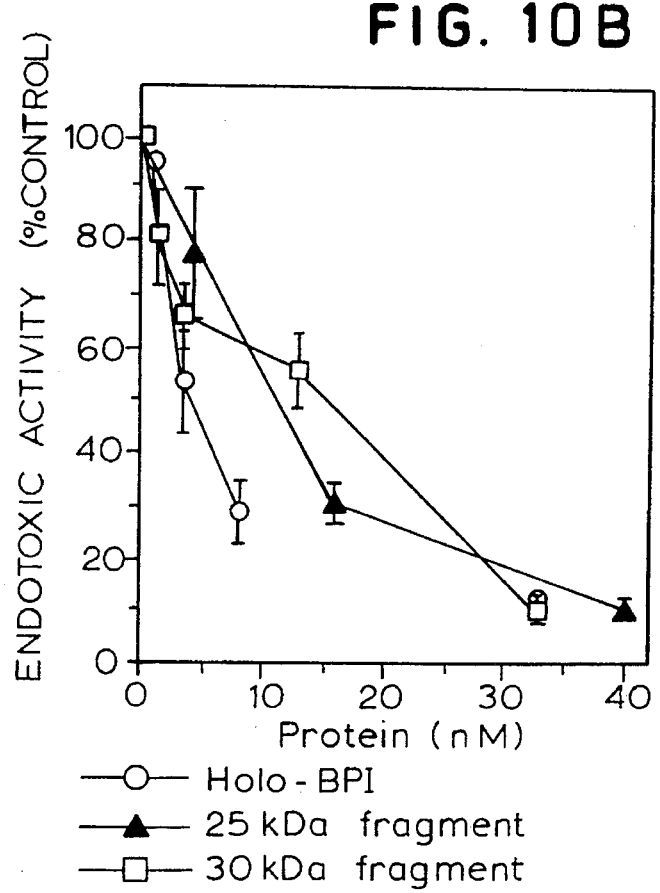

TNF production in whole human blood:

To determine if the potent endotoxin-neutralizing effects of BPI (and fragments), evident in a medium of artificial composition, could also be elicited in the complex environment of whole blood with its content of other LPS-binding proteins (such as LBP and lipoproteins), the effect of the proteins on the production of TNF in whole blood after incubation with LPS (Desch et al., supra) was examined. The results are shown in FIGS. 10A and 10B. Addition of LPS to whole blood triggers a dose-dependent synthesis and extracellular release of TNF (Desch et al., supra); as shown in FIG. 10A.

Addition of human BPI to whole human blood before adding $R_e595$ LPS caused a dose-dependent inhibition of TNF accumulation, over at least 30-fold range of LPS doses (0.1–3 ng/ml). At 1 ng/ml LPS, TNF production was inhibited by 50 percent at a BPI concentration of 4 nM and by approximately 90 percent at approximately 30 nM (FIG. 10B). As in the Limulus and the PMN-priming assays, the concentration dependence of the neutralizing activity of the 25 kD N-terminal fragment of human BPI was of the same order as that of holo-BPI, i.e., 50 percent inhibition at 12 nM and nearly 90 percent inhibition at 40 nM. However, in contrast to the weaker endotoxin-neutralizing activity in the preceding assays, the potency of the 30 kD C-terminal fragment(s) as an inhibitor of TNF production fell within the same range (50 percent inhibition of 15 nM protein and approximately 80 percent inhibition at approximately 30 nM) as shown for holo-BPI and the N-terminal framgent (FIG. 10B). Full inhibitory effects did not require preincubation of BPI (or fragments) with LPS. The proteins alone had no recognizable effect on TNF production in response to heat-killed *S. aureus* as shown in Table 4 below. The release of TNF in whole blood was measured as described above.

TABLE 4

BPI (fragments) do not inhibit TNF production
in whole blood triggered by heat-killed *S. auerus*

| Heat-killed *S. aureus* added | Protein added | | | |
|---|---|---|---|---|
| | None | Holo-BPI | 25 kD fragment | 30 kD fragment |
| | (TNF produced: ng/ml) | | | |
| $10^7$ | 1.5 | N.T.* | N.T. | N.T. |
| $3 \times 10^7$ | 3.8 | 4.1 | 3.4 | 3.9 |
| $10^8$ | 7.2 | 7.1 | 7.0 | 6.2 |
| $3 \times 10^8$ | 11.5 | 10.9 | 11.5 | 10.7 |

*N.T., not test

The finding that the C-terminal fragment of human BPI that lacks the charge properties for electrostatic attraction to LPS (net charge −2 to −3), but that contains several prominently hydrophobic regions (Gray, P. W., et al., *J. Biol. Chem.*, 264:9505, 1988), does not possess antibacterial properties but does exhibit LPS-neutralizing activity, suggest that its hydrophobic properties are sufficient for LPS recognition under certain conditions. Therefore, regions in the BPI molecule outside the N-terminal fragment can also contribute to interactions with LPS.

The LPS-neutralizing activity of the C-terminal fragment varies greatly with the different endpoints examined. Thus, whereas the C-terminal fragment shows no inhibition of the priming of PMN by $R_e595$ LPS, and very limited neutralizing activity in the Limulus assay (FIG. 6B) when the same "rough" LPS is the stimulus, with long chain LPS the C-terminal fragment is clearly inhibitory, although at molar concentrations that are much higher than of holo-BPI or the N-terminal fragment (FIG. 6a). On the other hand, the potency of the N-terminal and the C-terminal fragments as inhibitors of the stimulation of TNF production by LPS in whole blood in similar. Apparently, the highly variable physical presentation of LPS (Luderitz, O., et al., *Curr. Top. Membr. Transp.*, 17:79, 1982; Munford, R. S., et al., *J. Clin. Invest*, 70:878, 1982), depending on its chemical structure and state of aggregation as well as environmental factors such as ionic composition and neighboring macromolecules, has a much more profound effect on the LPS-interactive capabilities of the C-terminal fragment than of holo-BPI and the N-terminal fragment. The extent of LPS-neutralizing activity of the hydrophobic C-terminal fragment may depend on the accessibility of the fatty acyl chains of lipid A. These are shielded when LPS forms aggregates, especially in the case of "rough" LPS or within the hydrophobic bilayer of the intact bacterial envelope (Luderitz, O., et al., supra; Munford, R. S., et al., supra; Raetz, C. R. H., et al., *J. Biol. Chem.*, 265:1235, 1990), situations in which the C-terminal fragment shows little or no activity.

In summary, the above demonstrate that BPI can inhibit a number of LPS-dependent responses elicited by a variety of LPS. Without wishing to be bound by theory, it is most likely that both the endotoxin-neutralizing activity and the antibacterial action of BPI are initiated by binding of BPI to the endotoxin lipid A (and adjacent KDO) regions that are present in virtually all LPS. Acute phase sera contain a structurally related LPS-binding protein (LBP) that also appears to bind to this region of LPS (Tobias, P. S., Soldau, K., and Ulevitch, R. J., *J. Biol. Chem.*, 264:10867–10871, 1989). However, the biological properties of BPI and LBP are strikingly different: LBP has no antibacterial activity (Tobias, 1988, supra) and it amplifies rather than suppresses many LPS-triggered host responses (Wright, 1989, supra; Vosbeck, 1990, supra). Thus, binding to LPS per se does not necessarily lead to a particular biological effect, suggesting that the biological consequences depend on more subtle and specific aspects of protein-LPS interactions. The availability of cloned BPI protein and the identification of the active protein regions is expected to facilitate further dissection of the determinants of LPS recognition and neutralization in BPI.

What is claimed is:

1. A method for inhibiting the endotoxin-mediated release of Tumor Necrosis Factor in a mammal comprising administering to said mammal an effective amount of a peptide selected from the group consisting of a peptide having the amino acid sequence from about amino acid residue 200 to about amino acid residue 456 as set out in FIG. 5, a peptide having the amino acid sequence from about amino acid residue 204 to about amino acid residue 456 as set out in FIG. 5 and mixtures thereof.

2. A method for inhibiting cytokine-inducing effects of endotoxin in a mammal comprising administering to said mammal an effective amount of a peptide selected from the group consisting of a peptide having the amino acid sequence from about amino acid residue 200 to about amino acid residue 456 as set out in FIG. 5, a peptide having the amino acid sequence from about amino acid residue 204 to about amino acid residue 456 as set out in FIG. 5 and mixtures thereof.

* * * * *

UNITED STATES PATENT AND TRADEMARK OFFICE
CERTIFICATE OF CORRECTION

PATENT NO. : 5,576,292
DATED : November 19, 1996
INVENTOR(S) : Peter Elsbach and Jerrold Weiss It is certified that error appears in the above-identified patent and that said Letters Patent is hereby corrected as shown below:

Column 1, line 38, delete [chide] and substitute --crude--.

Column 1, line 66, delete [Patients] and substitute --patients--.

Column 8, line 39, delete [bum] and substitute --burn--.

Column 9, line 47, delete [CO.] and substitute --Co.--.

Column 11, line 15, after "granule insert "-".

Column 12, line 57, delete [frown] and substitute --from--.

Column 16, line 63, delete [52-5] and substitute --5205--.

Column 17, line 13, delete [Eco RI] and substitute --EcoRI--.

Column 17, line 21, delete [Eco RI] and substitute --EcoRI--.

Column 19, line 29, delete [1900] and substitute --1990--.

Column 19, line 66, after "produced" insert "a".

UNITED STATES PATENT AND TRADEMARK OFFICE
CERTIFICATE OF CORRECTION

PATENT NO. : 5,576,292
DATED : November 19, 1996
INVENTOR(S) : Peter Elsbach and Jerrold Weiss It is certified that error appears in the above-identified patent and that said Letters Patent is hereby corrected as shown below:

Column 21, line 3, delete [PMM] and substitute --PMN--.

Column 21, line 37, delete [printing] and substitute --priming--.

Signed and Sealed this

Seventeenth Day of November, 1998

Attest:

BRUCE LEHMAN

*Attesting Officer*      *Commissioner of Patents and Trademarks*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 1815 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens
        ( F ) TISSUE TYPE: blood
        ( G ) CELL TYPE: promyelocytic leukemia cells ( i x ) FEATURE:
        ( A ) NAME/KEY: misc_feature
        ( B ) LOCATION: 1813
        ( D ) OTHER INFORMATION: note=This sequence corresponds
            to Figure 5 in the application as filed. Note
            that the A at position 1813 corresponds to a poly A tail.

( x i ) SEQUENCE DESCRIPTION: SEQ ID NO:1:

```
CAGGCCTTGA  GGTTTTGGCA  GCTCTGGAGG  ATGAGAGAGA  ACATGGCCAG  GGGCCCTTGC     60
AACGCGCCGA  GATGGGTGTC  CCTGATGGTG  CTCGTCGCCA  TAGGCACCGC  CGTGACAGCG    120
GCCGTCAACC  CTGGCGTCGT  GGTCAGGATC  TCCCAGAAGG  GCCTGGACTA  CGCCAGCCAG    180
CAGGGGACGG  CCGCTCTGCA  GAAGGAGCTG  AAGAGGATCA  AGATTCCTGA  CTACTCAGAC    240
AGCTTTAAGA  TCAAGCATCC  TGGGAAGGGG  CATTATAGCT  TCTACAGCAT  GGAATCCCGT    300
GAATTCCAGC  TTCCCAGTTC  CCAGATAAGC  ATGGTGCCCA  ATGTGGGCCT  TAAGTTCTCC    360
ATCAGCAACG  CCAATATCAA  GATCAGCGGG  AAATGGAAGG  CACAAAAGAG  ATTCTTAAAA    420
ATGAGCGGCA  ATTTTGACCT  GAGCATAGAA  GGCATGTCCA  TTTCGGCTGA  TCTGAAGCTG    480
GGCAGTAACC  CCACGTCAGG  CAAGCCCACC  ATCACCTGCT  CCAGCTGCAG  CAGGCACATC    540
AACAGTGTCC  ACGTGCACAT  CTCAAAGAGC  AAAGTCGGGT  GGCTGATCCA  ACTCTTCCAC    600
AAAAAATTG   AGTCTGCGCT  TCGAAACAAG  ATGAACAGCC  AGGTCTGCGA  GAAAGTGACC    660
AATTCTGTAT  CCTCCAAGCT  GCAACCTTAT  TTCCAGACTC  TGCCAGTAAT  GACCAAAATA    720
GATTCTGTGG  CTGGAATCAA  CTATGGTCTG  GTGGCACCTC  CAGCAACCAC  GGCTGAGACC    780
CTGGATGTAC  AGATGAAGGG  GGAGTTTTAC  AGTGAGAACC  ACCACAATCC  ACCTCCCTTT    840
GCTCCACCAG  TGATGGAGTT  TCCCGCTGCC  CATGACCGCA  TGGTATACCT  GGGCCTCTCA    900
GACTACTTCT  TCAACACAGC  CGGGCTTGTA  TACCAAGAGG  CTGGGGTCTT  GAAGATGACC    960
CTTAGAGATG  ACATGATTCC  AAAGGAGTCC  AAATTTCGAC  TGACAACCAA  GTTCTTTGGA   1020
ACCTTCCTAC  CTGAGGTGGC  CAAGAAGTTT  CCCAACATGA  AGATACAGAT  CCATGTCTCA   1080
GCCTCCACCC  CGCCACACCT  GTCTGTGCAG  CCCACCGGCC  TTACCTTCTA  CCCTGCCGTG   1140
GATGTCCAGG  CCTTTGCCGT  CCTCCCCAAC  TCCTCCCTGG  CTTCCCTCTT  CCTGATTGGC   1200
ATGCACACAA  CTGGTTCCAT  GGAGGTCAGC  GCCGAGTCCA  ACAGGCTTGT  TGGAGAGCTC   1260
AAGCTGGATA  GGCTGCTCCT  GGAACTGAAG  CACTCAAATA  TTGGCCCCTT  CCCGGTTGAA   1320
```

```
TTGCTGCAGG ATATCATGAA CTACATTGTA CCCATTCTTG TGCTGCCCAG GGTTAACGAG      1380

AAACTACAGA AAGGCTTCCC TCTCCCGACG CCGGCCAGAG TCCAGCTCTA CAACGTAGTG      1440

CTTCAGCCTC ACCAGAACTT CCTGCTGTTC GGTGCAGACG TTGTCTATAA ATGAAGGCAC      1500

CAGGGGTGCC GGGGGCTGTC AGCCGCACCT GTTCCTGATG GGCTGTGGGG CACCGGCTGC      1560

CTTTCCCCAG GGAATCCTCT CCAGATCTTA ACCAAGAGCC CCTTGCAAAC TTCTTCGACT      1620

CAGATTCAGA AATGATCTAA ACACGAGGAA ACATTATTCA TTGGAAAAGT GCATGGTGTG      1680

TATTTTAGGG ATTATGAGCT TCTTTCAAGG GCTAAGGCTG CAGAGATATT TCTTCCAGGA      1740

ATCGTGTTTC AATTGTAACC AAGAAATTTC CATTTGTGCT TCATGAAAAA AAACTTCTGG      1800

TTTTTTTCAT GTGAA                                                      1815
```

( 2 ) INFORMATION FOR SEQ ID NO:2:

( i ) SEQUENCE CHARACTERISTICS:
        ( A ) LENGTH: 487 amino acids
        ( B ) TYPE: amino acid
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: Homo sapiens
        ( F ) TISSUE TYPE: blood
        ( G ) CELL TYPE: promyelocytic leukemia cells ( x i ) SEQUENCE DESCRIPTION: SEQ ID NO:2:

```
Met Arg Glu Asn Met Ala Arg Gly Pro Cys Asn Ala Pro Arg Trp Val
 1               5                  10                  15

Ser Leu Met Val Leu Val Ala Ile Gly Thr Ala Val Thr Ala Ala Val
                20                  25                  30

Asn Pro Gly Val Val Val Arg Ile Ser Gln Lys Gly Leu Asp Tyr Ala
            35                  40                  45

Ser Gln Gln Gly Thr Ala Ala Leu Gln Lys Glu Leu Lys Arg Ile Lys
        50                  55                  60

Ile Pro Asp Tyr Ser Asp Ser Phe Lys Ile Lys His Leu Gly Lys Gly
65                  70                  75                  80

His Tyr Ser Phe Tyr Ser Met Asp Ile Arg Glu Phe Gln Leu Pro Ser
                85                  90                  95

Ser Gln Ile Ser Met Val Pro Asn Val Gly Leu Lys Phe Ser Ile Ser
                100                 105                 110

Asn Ala Asn Ile Lys Ile Ser Gly Lys Trp Lys Ala Gln Lys Arg Phe
            115                 120                 125

Leu Lys Met Ser Gly Asn Phe Asp Leu Ser Ile Glu Gly Met Ser Ile
        130                 135                 140

Ser Ala Asp Leu Lys Leu Gly Ser Asn Pro Thr Ser Gly Lys Pro Thr
145                 150                 155                 160

Ile Thr Cys Ser Ser Cys Ser Ser His Ile Asn Ser Val His Val His
                165                 170                 175

Ile Ser Lys Ser Lys Val Gly Trp Leu Ile Gln Leu Phe His Lys Lys
                180                 185                 190

Ile Glu Ser Ala Leu Arg Asn Lys Met Asn Ser Gln Val Cys Glu Lys
            195                 200                 205

Val Thr Asn Ser Val Ser Ser Lys Leu Gln Pro Tyr Phe Gln Thr Leu
```

|     | 210 |     |     |     |     | 215 |     |     |     |     | 220 |     |     |     |
| --- | --- | --- | --- | --- | --- | --- | --- | --- | --- | --- | --- | --- | --- | --- |
| Pro 225 | Val | Met | Thr | Lys | Ile 230 | Asp | Ser | Val | Ala | Gly 235 | Ile | Asn | Tyr | Gly | Leu 240 |
| Val | Ala | Pro | Pro 245 | Ala | Thr | Thr | Ala | Glu | Thr 250 | Leu | Asp | Val | Gln | Met 255 | Lys |
| Gly | Glu | Phe | Tyr 260 | Ser | Glu | Asn | His | His 265 | Asn | Pro | Pro | Pro | Phe 270 | Ala | Pro |
| Pro | Val | Met 275 | Glu | Phe | Pro | Ala | Ala | His 280 | Asp | Arg | Met | Val 285 | Tyr | Leu | Gly |
| Leu | Ser 290 | Asp | Tyr | Phe | Phe | Asn 295 | Thr | Ala | Gly | Leu | Val 300 | Tyr | Gln | Glu | Ala |
| Gly 305 | Val | Leu | Lys | Met | Thr 310 | Leu | Arg | Asp | Asp | Met 315 | Ile | Pro | Lys | Glu | Ser 320 |
| Lys | Phe | Arg | Leu | Thr 325 | Thr | Lys | Phe | Phe | Gly 330 | Thr | Phe | Leu | Pro | Glu 335 | Val |
| Ala | Lys | Lys | Phe 340 | Pro | Asn | Met | Lys | Ile 345 | Gln | Ile | His | Val | Ser 350 | Ala | Ser |
| Thr | Pro | Pro 355 | His | Leu | Ser | Val | Gln 360 | Pro | Thr | Gly | Leu | Thr 365 | Phe | Tyr | Pro |
| Ala | Val 370 | Asp | Val | Gln | Ala | Phe 375 | Ala | Val | Leu | Pro | Asn 380 | Ser | Ser | Leu | Ala |
| Ser 385 | Leu | Phe | Leu | Ile | Gly 390 | Met | His | Thr | Thr | Gly 395 | Ser | Met | Glu | Val | Ser 400 |
| Ala | Glu | Ser | Asn | Arg 405 | Leu | Val | Gly | Glu | Leu 410 | Lys | Leu | Asp | Arg | Leu 415 | Leu |
| Leu | Glu | Leu | Lys 420 | His | Ser | Asn | Ile | Gly 425 | Pro | Phe | Pro | Val | Glu 430 | Leu | Leu |
| Gln | Asp | Ile 435 | Met | Asn | Tyr | Ile | Val 440 | Pro | Ile | Leu | Val | Leu 445 | Pro | Arg | Val |
| Asn | Glu 450 | Lys | Leu | Gln | Lys | Gly 455 | Phe | Pro | Leu | Pro | Thr 460 | Pro | Ala | Arg | Val |
| Gln 465 | Leu | Tyr | Asn | Val | Val 470 | Leu | Gln | Pro | His | Gln 475 | Asn | Phe | Leu | Leu | Phe 480 |
| Gly | Ala | Asp | Val | Val 485 | Tyr | Lys |     |     |     |     |     |     |     |     |     |

( 2 ) INFORMATION FOR SEQ ID NO:3:

( i ) SEQUENCE CHARACTERISTICS:
        ( A ) LENGTH: 221 amino acids
        ( B ) TYPE: amino acid
        ( D ) TOPOLOGY: linear ( i i ) MOLECULE TYPE: protein ( i i i ) HYPOTHETICAL: YES ( i v ) ANTI-SENSE: NO ( v ) FRAGMENT TYPE: C-terminal ( v i ) ORIGINAL SOURCE:
        ( A ) ORGANISM: Homo sapiens
        ( G ) CELL TYPE: blood
        ( H ) CELL LINE: promyelocytic leukemia cells ( x i ) SEQUENCE DESCRIPTION: SEQ ID NO:3:

| Val 1 | Asn | Pro | Gly | Val 5 | Val | Val | Arg | Ile | Ser 10 | Gln | Lys | Gly | Leu | Asp 15 | Tyr |
| --- | --- | --- | --- | --- | --- | --- | --- | --- | --- | --- | --- | --- | --- | --- | --- |
| Ala | Ser | Gln | Gln | Gly Thr | Ala | Ala | Leu | Gln | Lys | Glu | Leu | Lys | Arg | Ile |

|          |     |     |     |     |     | 20  |     |     |     |     | 25  |     |     |     |     | 30  |     |     |     |
|----------|-----|-----|-----|-----|-----|-----|-----|-----|-----|-----|-----|-----|-----|-----|-----|-----|-----|-----|-----|

Lys Ile Pro Asp Tyr Ser Asp Ser Phe Lys Ile Lys His Leu Gly Lys
        35                      40                  45

Gly His Tyr Ser Phe Tyr Ser Met Asp Ile Arg Glu Phe Gln Leu Pro
    50                  55                  60

Ser Ser Gln Ile Ser Met Val Pro Asn Val Gly Leu Lys Phe Ser Ile
65              70                  75                      80

Ser Asn Ala Asn Ile Lys Ile Ser Gly Lys Trp Lys Ala Gln Lys Arg
                85              90                      95

Phe Leu Lys Met Ser Gly Asn Phe Asp Leu Ser Ile Glu Gly Met Ser
            100             105             110

Ile Ser Ala Asp Leu Lys Leu Gly Ser Asn Pro Thr Ser Gly Lys Pro
        115             120             125

Thr Ile Thr Cys Ser Ser Cys Ser Ser His Ile Asn Ser Val His Val
    130             135             140

His Ile Ser Lys Ser Lys Val Gly Trp Leu Ile Gln Leu Phe His Lys
145             150             155             160

Lys Ile Glu Ser Ala Leu Arg Asn Lys Met Asn Ser Gln Val Cys Glu
                165             170             175

Lys Val Thr Asn Ser Val Ser Ser Lys Leu Gln Pro Tyr Phe Gln Thr
            180             185             190

Leu Pro Val Met Thr Lys Ile Asp Ser Val Ala Gly Ile Asn Tyr Gly
        195             200             205

Leu Val Ala Pro Pro Ala Thr Thr Ala Glu Thr Leu Asp
    210             215             220

( 2 ) INFORMATION FOR SEQ ID NO:4:

( i ) SEQUENCE CHARACTERISTICS:
        ( A ) LENGTH: 658 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens
        ( G ) CELL TYPE: blood
        ( H ) CELL LINE: promyelocytic leukemia cells ( x i ) SEQUENCE DESCRIPTION: SEQ ID NO:4:

| | | | | | |
|---|---|---|---|---|---|
| CGTCAACCCT | GGCGTCGTGG | TCAGGATCTC | CCAGAAGGGC | CTGGACTACG | CCAGCCAGCA | 60 |
| GGGGACGGCC | GCTCTGCAGA | AGGAGCTGAA | GAGGATCAAG | ATTCCTGACT | ACTCAGACAG | 120 |
| CTTTAAGATC | AAGCATCCTG | GGAAGGGGCA | TTATAGCTTC | TACAGCATGG | AATCCGTGA  | 180 |
| ATTCCAGCTT | CCCAGTTCCC | AGATAAGCAT | GGTGCCCAAT | GTGGGCCTTA | AGTTCTCCAT | 240 |
| CAGCAACGCC | AATATCAAGA | TCAGCGGGAA | ATGGAAGGCA | CAAAAGAGAT | TCTTAAAAAT | 300 |
| GAGCGGCAAT | TTTGACCTGA | GCATAGAAGG | CATGTCCATT | TCGGCTGATC | TGAAGCTGGG | 360 |
| CAGTAACCCC | ACGTCAGGCA | AGCCCACCAT | CACCTGCTCC | AGCTGCAGCA | GGCACATCAA | 420 |
| CAGTGTCCAC | GTGCACATCT | CAAAGAGCAA | AGTCGGGTGG | CTGATCCAAC | TCTTCCACAA | 480 |
| AAAAATTGAG | TCTGCGCTTC | GAAACAAGAT | GAACAGCCAG | GTCTGCGAGA | AGTGACCAA  | 540 |
| TTCTGTATCC | TCCAAGCTGC | AACCTTATTT | CCAGACTCTG | CCAGTAATGA | CCAAAATAGA | 600 |

TTCTGTGGCT GGAATCAACT ATGGTCTGGT GGCACCTCCA GCAACCACGG CTGAGACC  658

( 2 ) INFORMATION FOR SEQ ID NO:5:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Homo sapiens
        ( G ) CELL TYPE: blood
        ( H ) CELL LINE: polymorphonuclear lymphocytes ( x i ) SEQUENCE DESCRIPTION: SEQ ID NO:5:

```
Val Asn Pro Gly Val Val Arg Ile Ser Gln Lys Gly Leu Asp Tyr
 1               5                  10                  15
Ala Ser Gln Gln
         20
```

( 2 ) INFORMATION FOR SEQ ID NO:6:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( i x ) FEATURE:
        ( A ) NAME/KEY: misc_feature
        ( B ) LOCATION: 1..56
        ( D ) OTHER INFORMATION: note=This sequence can be found
            in the application, as filed on page 25, line 28.

( x ) PUBLICATION INFORMATION:
        ( A ) AUTHORS: Ooi, C. E. et al.
        ( C ) JOURNAL: J. Biol. Chem.
        ( D ) VOLUME: 262
        ( F ) PAGES: 14891-14894
        ( G ) DATE: 1987

( x i ) SEQUENCE DESCRIPTION: SEQ ID NO:6:

GTCAATCCTG GTGTTGTGGT CAGGATCTCT CAGAAGGGCC TGGATTATGC CTCCCA  56

( 2 ) INFORMATION FOR SEQ ID NO:7:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( i x ) FEATURE:
        ( A ) NAME/KEY: misc_feature -continued (B) LOCATION: 1..55
(D) OTHER INFORMATION: note=This sequence can be found
    in the application, as filed, on page 25, line
    29.

(x) PUBLICATION INFORMATION:
    (A) AUTHORS: Ooi, C. E. et al.
    (C) JOURNAL: J. Biol. Chem.
    (D) VOLUME: 262
    (F) PAGES: 14891-14894
    (G) DATE: 1987

(xi) SEQUENCE DESCRIPTION: SEQ ID NO:7:

GCAAGGCACA GCTGCCCTGC AGAAGGAGCT GAAGAGGATC AAGATTCCTG ACTAT    55